US009458481B2

(12) United States Patent
Winzer et al.

(10) Patent No.: US 9,458,481 B2
(45) Date of Patent: Oct. 4, 2016

(54) METHYLTRANSFERASE NUCLEIC ACIDS AND POLYPEPTIDES

(75) Inventors: Thilo Hans Winzer, York (GB); Tracy Carol Walker, Latrobe (AU); Ian Alexander Graham, York (GB)

(73) Assignee: Sun Pharmaceutical Industries (Australia) Pty Ltd, Notting Hill (AT)

( * ) Notice: Subject to any disclaimer, the term of this patent is extended or adjusted under 35 U.S.C. 154(b) by 591 days.

(21) Appl. No.: 13/806,310

(22) PCT Filed: Jun. 16, 2011

(86) PCT No.: PCT/GB2011/051121
§ 371 (c)(1), (2), (4) Date: Dec. 21, 2012

(87) PCT Pub. No.: WO2011/161431
PCT Pub. Date: Dec. 29, 2011

(65) Prior Publication Data

US 2013/0104258 A1 Apr. 25, 2013

(30) Foreign Application Priority Data

Jun. 22, 2010 (GB) .................................. 1010471.9
Dec. 22, 2010 (GB) .................................. 1021720.6

(51) Int. Cl.
*C07K 14/415* (2006.01)
*C12P 17/18* (2006.01)
*C12N 9/10* (2006.01)
*C12N 15/82* (2006.01)

(52) U.S. Cl.
CPC ............ *C12P 17/188* (2013.01); *C07K 14/415* (2013.01); *C12N 9/1007* (2013.01); *C12N 15/8243* (2013.01); *C12Y 201/01* (2013.01)

(58) Field of Classification Search
CPC ................................. C12P 17/18; C12N 9/10
See application file for complete search history.

(56) References Cited

U.S. PATENT DOCUMENTS

| | | | | |
|---|---|---|---|---|
| 7,390,642 | B2 | 6/2008 | Kutchan et al. | |
| 2005/0106588 | A1* | 5/2005 | Kutchan et al. .................. | 435/6 |
| 2007/0199090 | A1* | 8/2007 | Apuya et al. ................. | 800/278 |
| 2008/0196123 | A1 | 8/2008 | Kutchan et al. | |
| 2009/0227796 | A1* | 9/2009 | Fist .......................... | A01H 5/02 546/44 |
| 2010/0075385 | A1* | 3/2010 | Kutchan ............ | C12N 15/8243 435/122 |

(Continued)

FOREIGN PATENT DOCUMENTS

| | | | |
|---|---|---|---|
| EP | 1 270 727 | A1 | 1/2003 |
| EP | 1 512 748 | A1 | 3/2005 |

(Continued)

OTHER PUBLICATIONS

Evertsz, E. M et al. "Research Report Hybridization Cross-Reactivity within Homolo-gous Gene Families on Glass cDNA Microarrays." Biotechniques 31.5 (2001): 1182-1192.*

(Continued)

*Primary Examiner* — Russell Kallis
*Assistant Examiner* — Weihua Fan
(74) *Attorney, Agent, or Firm* — Klarquist Sparkman, LLP

(57) ABSTRACT

This disclosure relates to the isolation and sequencing of nucleic acid molecules that encode methyltransferase polypeptides from a *Papaver somniferum* cultivar; and uses in the production of noscapine and identification of poppy cultivars that include the genes that include these nucleic acid molecules.

37 Claims, 12 Drawing Sheets

```
ATGGCTACCAATGGCGAAATTTTCAATACCTATGGTCATAATCATCAATCAGCCACAGTCACTAAAATCACTGCT
TCTAATGAAAGCAGCAATGGTGTCTGTTATCTTTCAGAAACGGCTAACTTGGGGAAGTTAATATGCATTCCAATG
GCACTAAGAGCTGCGATGGAGCTAAATGTGTTCCAACTTATCTCAAAGTTCGGAACTGACGCAAAAGTTTCGGCT
TCTGAAATTGCCTCTAAAATGCCAAACGCGAAGAATAATCCTGAAGCAGCTATGTATTTGGATAGAATTCTTCGA
CTGCTCGGGGCAAGTTCTATTCTTTCTGTTTCTACTACAAAAAAATCAATCAACAGAGGAGGAGATGATGTAGTA
GTACATGAGAAGCTTTATGGGTTAACAAATTCGTCGTGTTGTTTGGTCCCTCGACAAGAAGACGGGGTGTCATTA
GTCGAAGAATTGCTATTCACATCTGACAAGGTTGTTGTGGATAGTTTTTTCAAACTGAAATGTGTGGTGGAAGAA
AAAGACAGTGTGCCATTTGAGGTTGCTCATGGTGCTAAAATCTTTGAGTATGCTGCTACAGAACCAAGAATGAAT
CAAGTATTTAACGATGGAATGGCAGTTTTCTCTATTGTTGTTTTTGAGGCTGTTTTTAGAGTTTACGATGGATTT
CTTGATATGAAAGAATTGTTAGATGTTGGTGGTGGTATTGGTACTTCGGTTAGTAAGATTGTTGCTAAATACCCT
TTGATTCGCGGTGTCAACTTCGACTTGCCTCATGTTATTTCTGTTGCCCCTCAATACCCAGGTGTAGAGCATGTT
GCAGGAGATATGTTCGAGGAAGTCCCAAAGGGTCAAAACATGTTGCTAAAATGGGTACTGCACGATTGGGGTGAT
GAACGATGTGTGAAGCTGTTAAAGAATTGTTGGAACTCATTACCTGTGGGTGGAAAAGTTTTGATAATCGAGTTT
GTTCTCCCGAATGAACTTGGTAACAATGCTGAATCATTCAATGCGTTGATTCCCGATTTACTCCTGATGGCTCTG
AATCCAGGCGGTAAAGAGCGAACGATTTCCGAATACGATGATTTAGGCAAAGCAGCTGGATTCATAAAAACTATA
CCTATCCCTATCTCCAATGGTCTTCATGTCATTGAGTTTCACAAATGA
```

```
ATGGAAATTCATTTAGAAAGCCAAGAACAAGAAATGAAATATCAATCTCAAATCTGGAACCAAATATGTGGCACT
GTTGATACCTCTGTTCTGAGATGTGCAATTCAATTAGGTATATTTGATGCCATTCATAACTCTGGCAAACCAATG
ATTACCTTAACCGAATTATCAAGCATTGTTTCATCACCCTCTTCATCTTCAATCGAACCCTGCAACTTGTATAGA
TTAGTGAGATACTTATCCCAAATGGATCTCATTAGTATCGGAGAATGTTTGAATGAAGCAACTGTTTCATTAACA
GGCACATCCAAGTTACTACTTAGAAACCAAGAAAAGAGTTTAATTGATTGGGTATTGGCAATTTCTTGCGAAATG
ATGGTTGTTGTTTGGCACGAACTAAGTAGCTCTGTTTCAACTCCTGCGGATGAGCCTCCAATCTTCCAGAAGGTT
CATGGTAAAAATGCTTTAGAATTAGCAGGGGAATTTCCAGAATGGAATGATCTGATCAACAATGCTATGACTAGT
GATACTAGTGTAACTAAGCCAGCGCTAATACAAGGATGTGGCAAAATCCTGAACGGAGTTACATCGTTAATTGAT
GTCGGTGGTGGTCACGGTGCCACTATGGCCTACATAGTTGAAGCTTTTCCTCACATAAAAGGTGCGGTAATCGAT
TTACCACATGTTGTTGAAGCCGCTCCGGAGCGTCCAGGTGTTGAGTTCATCAGCGGTGATATATTCAAGTCCATT
TCTAACGCTGATGCTGTGTTGTTGAAGTATGTCCTGCACAATTGGGAAGATACGGAATGTGTGAATTTACTGAAG
AGATGTAAGGAAGCAGTTCCGGCAGACAAAGGAAAAGTGATCATAATGGATTTAGTAATAGACGACGATGATAAC
AGTATTTTAACGCAGGCAAAGTTGAGCCTTGATCTCACTGTGATGAACCATGGAGGAGGTAGAGAAAGGACTAAA
GAAGATTGGAGAAATCTAATTGAGATGTCTGGATTTAGTAGGCATGAAATAATTCCAATATCTGCCATGCCATCA
ATTATTGTTGCTTATCCTTAG
```

(56) References Cited

U.S. PATENT DOCUMENTS

| | | | | |
|---|---|---|---|---|
| 2010/0184166 | A1* | 7/2010 | Sato et al. | 435/122 |
| 2013/0133105 | A1 | 5/2013 | Winzer et al. | |
| 2015/0004659 | A1 | 1/2015 | Winzer et al. | |

FOREIGN PATENT DOCUMENTS

| | | | |
|---|---|---|---|
| EP | 1 632 565 | A1 | 3/2006 |
| EP | 1 837 396 | A1 | 9/2007 |
| WO | WO 99/14351 | A1 | 3/1999 |
| WO | WO 02/101052 | A2 | 12/2002 |
| WO | WO 2006/081029 | A2 | 8/2006 |
| WO | WO 2006/138012 | A1 | 12/2006 |
| WO | WO 2008/069878 | A2 | 6/2008 |
| WO | WO 2009/005647 | A2 | 1/2009 |
| WO | WO 2009/064771 | A2 | 5/2009 |
| WO | WO 2011/161431 | A2 | 12/2011 |
| WO | WO 2012/010872 | A2 | 1/2012 |
| WO | WO 2013/136057 | A2 | 9/2013 |

OTHER PUBLICATIONS

Allen, Robert S., et al. "Metabolic engineering of morphinan alkaloids by over-expression and RNAi suppression of salutaridinol 7-O-acetyltransferase in opium poppy." Plant biotechnology journal 6.1 (2008): 22-30.*
Hileman, Lena C., et al. "Virus-induced gene silencing is an effective tool for assaying gene function in the basal eudicot species *Papaver somniferum* (opium poppy)." The Plant Journal 44.2 (2005): 334-341.*
Till, Bradley J., et al. "Mismatch cleavage by single-strand specific nucleases." Nucleic Acids Research 32.8 (2004): 2632-2641.*
Allen, R. S., et al., 2008, Plant biotechnology journal 6(1): 22-30.*
Hileman, L.C., et al., 2005, The Plant Journal 44(2): 334-341.*
Till, B.J., et al., 2004, Nucleic Acids Research 32(8): 2632-2641.*
GenBank Accession No. AK320249.1, published May 1, 2010.
GenBank Accession No. BT096188.1, published Aug. 6, 2009.
GenBank Accession No. EU882980.1, published Nov. 13, 2009.
New Zealand Patent Office, Further Examination Report, dated Sep. 15, 2014 (2 pages).
Nucleic acid sequence alignment between GenBank Accession No. AK320249.1 and methyltransferase PSMT2 sequence of the current application (SEQ ID No. 2).
Nucleic acid sequence alignment between GenBank Accession No. BT096188.1 and methyltransferase PSMT2 sequence of the current application (SEQ ID No. 2).
Nucleic acid sequence alignment between GenBank Accession No. EU882980.1 and methyltransferase PSMT2 sequence of the current application (SEQ ID No. 2).
Amino acid sequence alignment between GenBank Accession No. AK320249.1 and methyltransferase PSMT2 sequence of the current application (SEQ ID No. 8).
Amino acid sequence alignment between GenBank Accession No. BT096188.1 and methyltransferase PSMT2 sequence of the current application (SEQ ID No. 8).
Amino acid sequence alignment between GenBank Accession No. EU882980.1 and methyltransferase PSMT2 sequence of the current application (SEQ ID No. 8).
GenBank Accession No. CAG34222.1, Jun. 14, 2004.
Accession No. AB126256, May 10, 2005.
Accession No. AB126257, May 10, 2005.
Database UniProt [Online] Accession No. Q0ZPV6, Aug. 22, 2006.
Accession No. AB374409, Jan. 10, 2008.
Accession No. A9ZT62, Feb. 26, 2008.
Database UniProt [Online] Accession No. B9SK36, Mar. 24, 2009.
Accession No. GU325750, Jan. 28, 2010.
Accession No. D3JXF8, Mar. 23, 2010.
Chan et al., "Draft Genome Sequence of the Oilseed Species *Ricinus communis*," *Nat Biotechnol.* 28:951-959, 2010.
Chávez et al., "Characterization of Two Methylenedioxy Bridge-Forming Cytochrome P450-Dependent Enzymes of Alkaloid Formation in the Mexican Prickly Poppy *Argemone mexica*," *Arch. Biochem. Biophys.* 507:186-193, 2011.
Chu et al., "From Hormones to Secondary Metabolism: The Emergence of Metabolic Gene Clusters in Plants," *Plant J.* 66:66-79, 2011.
Desgagné-Penix et al., "Integration of Deep Transcriptome and Proteome Analyses Reveals the Components of Alkaloid Metabolism in Opium Poppy Cell Cultures," *BMC Plant Biol.* 10:252, 2010.
Facchini et al., "Opium Poppy: Blueprint for an Alkaloid Factory," *Phytochem Rev.* 6:97-124, 2007.
Facchini and De Luca, "Opium Poppy and Madagascar Periwinkle: Model Non-Model Systems to Investigate Alkaloid Biosynthesis in Plants," *Plant J.* 54:763-784, 2008.
Field et al., "Formation of Plant Metabolic Gene Clusters Within Dynamic Chromosomal Regions," *Proc Natl Acad Sci.* 108:16116-16121, 2011.
Frick et al., "Metabolic Engineering with a Morphine Biosynthetic P450 in Opium Poppy Surpasses Breeding," *Metabolic Eng.* 9:169-176, 2007.
Gesell et al., "CYP719B1 is Salutaridine Synthase, the C—C Phenol-Coupling Enzyme of Morphine Biosynthesis in Opium Poppy," *J. Biol. Chem.* 284:24432-24442, 2009.
Great Britain Search Report dated Oct. 15, 2010 for Great Britain Application No. GB1010471.9.
Great Britain Search Report dated Nov. 23, 2010 for Great Britain Application No. GB1012262.0.
Great Britain Search Report dated Jul. 2, 2012 for Great Britain Application No. GB1204407.9 (PSMT1).
Great Britain Search Report dated Oct. 1, 2012 for Great Britain Application No. GB1204407.9 (CYP82Y1).
Great Britain Search Report dated Oct. 1, 2012 for Great Britain Application No. GB1204407.9 (PSSDR1).
Great Britain Search Report dated Oct. 31, 2012 for Great Britain Application No. GB1204407.9 (PSATI).
Great Britain Search Report dated Oct. 31, 2012 for Great Britain Application No. GB1204407.9 (PSCXE1).
Hagel et al., "Quantitative $^1$H Nuclear Magnetic Resonance Metabolite Profiling as a Functional Genomics Platform to Investigate Alkaloid Biosynthesis in Opium Poppy," *Plant Physiol.* 147:1805-1821, 2008.
Hileman et al., "Virus-Induced Gene Silencing is an Effective Tool for Assaying Gene Function in the Basal Eudicot Species *Papaver somniferum* (Opium Poppy)," *Plant J.* 44:334-341, 2005.
Ikezawa et al., "Molecular Cloning and Characterization of Methylenedioxy Bridge-Forming Enzymes Involved in Stylopine Biosynthesis in *Eschscholzia californica*," *FEBS J* . 274:1019-1035, 2007.
Kleber da Rocha et al., "Effect of Different Culture Medium Components on Production of Alkaloid in Callus Tissues of *Cereus Peruvianus* (Cactaceae)," *Acta Scientiarum Biol. Sci.* 27:37-41, 2005.
Okada, "The Biosynthesis of Isoprenoids and the Mechanisms Regulating it in Plants," *Biosci Biotechol Biochem.* 75:1219-1225, 2011.
Takos et al., "Genomic Clustering of Cyanogenic Glucoside Biosynthetic Genes Aids Their Identification in *Lotus japonicus* and Suggests the Repeated Evolution of this Chemical Defence Pathway," *Plant J.* 68:273-286, 2011.
Wesley et al., "Construct Design for Efficient, Effective and High-Throughput Gene Silencing in Plants," *Plant J.* 27:581-590, 2001.
Wijekoon and Facchini, "Systematic Knockdown of Morphine Pathway Enzymes in Opium Poppy Using Virus-Induced Gene Silencing," *Plant J.* 69:1052-1063, 2012.
Ziegler et al., "Comparative Transcrpt and Alkaloid Profiling in Papaver Species Identifies a Short Chain Dehydrogenase/Reductase Involved in Morphine Biosynthesis," *Plant J.* 48:177-192, 2006.
Ziegler et al., "Evolution of Morphine Biosynthesis in Opium Poppy," *Phytochem.* 70:1696-1707, 2009.
Decker et al., "Characterization of Proteins in Latex of the Opium Poppy (*Papaver somniferum*) Using Two-Dimensional Gel Electrophoresis and Microsequencing," *Electrophoresis 21*:3500-3516, 2000.

(56) References Cited

OTHER PUBLICATIONS

Facchini et al., "Developmental and Inducible Accumulation of Gene Transcripts Involved in Alkaloid Biosynthesis in Opium Poppy," *Phytochemistry 64*:177-186, 2003.
Liscombe and Facchini, "Molecular Cloning and Characterization of Tetrahydroprotoberberine cis-N-Methyltransferase, an Enzyme Involved in Alkaloid Biosynthesis in Opium Poppy," *J. Biol. Chem.* 282:14741-14751, 2007.
Morishige et al., "Molecular Characterization of the S-adenosyl-L-methionine:3'-Hydroxy-N-methylcoclaurine 4'-O-Methyltransferase Involved in Isoquinoline Alkaloid Biosynthesis in *Coptis japonica,*" *J. Biol. Chem.* 275:23398-23405, 2000.
Ounaroon et al., "(R,S)-Reticuline 7-O-methyltransferase and (R,S)-nor coclaurine 6-O-methyltransferase of *Papaver somniferum*—cDNA Cloning and Characterization of Methyl Transfer Enzymes of Alkaloid Biosynthesis in Opium Poppy," *Plant J.* 36:808-819, 2003.
Winzer et al., "A *Papaver somniferum* 10-Gene Cluster for Synthesis of the Anticancer Alkaloid Noscapine," *Science 336*:1704-1708, 2012.
Ziegler et al., "Comparative Macroarray Analysis of Morphine Containing *Papaver somniferum* and Eight Morphine Free *Papaver* Species Identifies an O-methyltransferase Involved in Benzylisoquinoline Biosynthesis," *Planta 222*:458-471, 2005.
Omura and Sato, "The Carbon Monoxide-Binding Pigment of Liver Microsomes. I. Evidence for Its Hemoprotein Nature," *J Bio Chem.* 239:2370-2378, 1964.
Sato et al., "S-Adenosyl-L-Methionine: Scoulerine-9-O-Methyltransferase from Cultured *Coptis Japonica* Cells" *Phytochem.* 32:659-664, 1993.
Gümüşçü et al., "Evaluation of Selected Poppy (*Papaver somniferum* L.) Lines by Their Morphine and Other Alkaloids Contents," *Eur Food Res Technol.* 226:1213-1220, 2008.
Pienkny et al., "Functional Characterization of a Novel Benzylisoquinoline O-Methyltransferase Suggests Its Involvement in Papaverine Biosynthesis in Opium Poppy (*Papaver somniferum* L)," *Plant J.* 60:56-67, 2009.
Schuler and Werck-Reichhart, "Functional Genomics of P450s," *Annu Rev Plant Biol.* 54:629-667, 2003.
International Search Report and Written Opinion of the International Searching Authority for corresponding PCT Application No. PCT/GB2011/051340, dated Feb. 8, 2012.

* cited by examiner

Figure 1a

ATGGCTACCAATGGCGAAATTTTCAATACCTATGGTCATAATCATCAATCAGCCACAGTCACTAAAATCACTGCT
TCTAATGAAAGCAGCAATGGTGTCTGTTATCTTTCAGAAACGGCTAACTTGGGGAAGTTAATATGCATTCCAATG
GCACTAAGAGCTGCGATGGAGCTAAATGTGTTCCAACTTATCTCAAAGTTCGGAACTGACGCAAAAGTTTCGGCT
TCTGAAATTGCCTCTAAAATGCCAAACGCGAAGAATAATCCTGAAGCAGCTATGTATTTGGATAGAATTCTTCGA
CTGCTCGGGGCAAGTTCTATTCTTTCTGTTTCTACTACAAAAAAATCAATCAACAGAGGAGGAGATGATGTAGTA
GTACATGAGAAGCTTTATGGGTTAACAAATTCGTCGTGTTGTTTGGTCCCTCGACAAGAAGACGGGGTGTCATTA
GTCGAAGAATTGCTATTCACATCTGACAAGGTTGTTGTGGATAGTTTTTTCAAACTGAAATGTGTGGTGGAAGAA
AAAGACAGTGTGCCATTTGAGGTTGCTCATGGTGCTAAAATCTTTGAGTATGCTGCTACAGAACCAAGAATGAAT
CAAGTATTTAACGATGGAATGGCAGTTTTCTCTATTGTTGTTTTTGAGGCTGTTTTTAGAGTTTACGATGGATTT
CTTGATATGAAAGAATTGTTAGATGTTGGTGGTGGTATTGGTACTTCGGTTAGTAAGATTGTTGCTAAATACCCT
TTGATTCGCGGTGTCAACTTCGACTTGCCTCATGTTATTTCTGTTGCCCCTCAATACCCAGGTGTAGAGCATGTT
GCAGGAGATATGTTCGAGGAAGTCCCAAAGGGTCAAAACATGTTGCTAAAATGGGTACTGCACGATTGGGGTGAT
GAACGATGTGTGAAGCTGTTAAAGAATTGTTGGAACTCATTACCTGTGGGTGGAAAAGTTTTGATAATCGAGTTT
GTTCTCCCGAATGAACTTGGTAACAATGCTGAATCATTCAATGCGTTGATTCCCGATTTACTCCTGATGGCTCTG
AATCCAGGCGGTAAAGAGCGAACGATTTCCGAATACGATGATTTAGGCAAAGCAGCTGGATTCATAAAAACTATA
CCTATCCCTATCTCCAATGGTCTTCATGTCATTGAGTTTCACAAATGA

Figure 1b

ATGGAAATTCATTTAGAAAGCCAAGAACAAGAAATGAAATATCAATCTCAAATCTGGAACCAAATATGTGGCACT
GTTGATACCTCTGTTCTGAGATGTGCAATTCAATTAGGTATATTTGATGCCATTCATAACTCTGGCAAACCAATG
ATTACCTTAACCGAATTATCAAGCATTGTTTCATCACCCTCTTCATCTTCAATCGAACCCTGCAACTTGTATAGA
TTAGTGAGATACTTATCCCAAATGGATCTCATTAGTATCGGAGAATGTTTGAATGAAGCAACTGTTTCATTAACA
GGCACATCCAAGTTACTACTTAGAAACCAAGAAAAGAGTTTAATTGATTGGGTATTGGCAATTTCTTGCGAAATG
ATGGTTGTTGTTTGGCACGAACTAAGTAGCTCTGTTTCAACTCCTGCGGATGAGCCTCCAATCTTCCAGAAGGTT
CATGGTAAAAATGCTTTAGAATTAGCAGGGGAATTTCCAGAATGGAATGATCTGATCAACAATGCTATGACTAGT
GATACTAGTGTAACTAAGCCAGCGCTAATACAAGGATGTGGCAAAATCCTGAACGGAGTTACATCGTTAATTGAT
GTCGGTGGTGGTCACGGTGCCACTATGGCCTACATAGTTGAAGCTTTTCCTCACATAAAAGGTGCGGTAATCGAT
TTACCACATGTTGTTGAAGCCGCTCCGGAGCGTCCAGGTGTTGAGTTCATCAGCGGTGATATATTCAAGTCCATT
TCTAACGCTGATGCTGTGTTGTTGAAGTATGTCCTGCACAATTGGGAAGATACGGAATGTGTGAATTTACTGAAG
AGATGTAAGGAAGCAGTTCCGGCAGACAAAGGAAAAGTGATCATAATGGATTTAGTAATAGACGACGATGATAAC
AGTATTTTAACGCAGGCAAAGTTGAGCCTTGATCTCACTGTGATGAACCATGGAGGAGGTAGAGAAAGGACTAAA
GAAGATTGGAGAAATCTAATTGAGATGTCTGGATTTAGTAGGCATGAAATAATTCCAATATCTGCCATGCCATCA
ATTATTGTTGCTTATCCTTAG

Figure 1c

ATGGAAGTAGTAAGTAAGATTGATCAAGAAAACCAAGCAAAAATTTGGAAACAAATTTTTGGTTTTGCAGAATCA
TTAGTTCTAAAATGTGCAGTTCAGTTAGAGATTGCTGAAACACTTCATAATAATGTAAAACCCATGTCTTTATCC
GAGTTAGCATCTAAACTTCCGGCTCAACCCGTTAATGAAGACCGTTTGTACCGAATTCTGCATTTCTTAGTTCAC
ATGAAACTCTTCAACAAAGATGCTACCACACAGAAATATTCATTAGCTCCACCAGCAAAGTATTTGCTAAAAGGC
TGGGAAAAATCAATGGTTCCTTCAATATTAAGCGTGACTGATAAAGATTTTACAGCTCCATGGAATCATCTTGGG
GACGGTTTAACCGGTAACTGTAACGCTTTTGAGAAAGCGTTAGGAAAGGGCATTCGGGTTTATATGAGAGAAAAT
CCTGAAAAAGATCAATTGTTTAATGAAGGAATGGCTTGTGATACTAGATTATTTGCTTCAGCATTGGTTAACGAG
TGCAAAAGTATTTTCAGTGACGGGATCAATACACTTGCCGGTGTTGGCCGTGGTACTGGTACTGCAGTGAAAGCC
ATATCCAAAGCTTTTCCGGATATTAAGTGCACAATCCATGATCTTCCTGAAGTTACCAGTAAAAATAGTAAAATT
CCAAGAGATGTTTTTAAGTCCGTTCCTAGTGCAGACGCCATCTTTATGAAGAGCATTCTTCACGAATGGAACGAT
GAGGAATGTATTCAAATCTTGAAACGATGCAAAGAAGCAATACCAAAAGGGGGCAAAGTTATCATTGCGGATGTC
GTAATAGACATGGACTCGACTCATCCGTATTCAAAATCTAGACTCGCAATGGATTTGGCTATGATGCTCCACACG
GGTGGAAAAGAGAGAACTGAAGAAGATTGGAAAAAACTTATTGATGCTGCAGGTTTTGCTAGCTGTAAAATTACT
AAACTATCTGCTCTCCAGTCTGTTATTGAGGCTTACCCTCATTGA

Figure 3a

| Start | End | Feature |
|---|---|---|
| 1 | 66 | 5′ untranslated region |
| 67 | 877 | exon 1 |
| 878 | 993 | intron 1 |
| 994 | 1058 | exon 2 |
| 1059 | 1841 | intron 2 |
| 1842 | 2138 | exon 3 |
| 2139 | 2306 | 3′ untranslated region |

CACACCAAACTTGATCATTGTCATAAAAAACAGTCCTAATTGTCATCAATCAAAAACAGTCCTAACATGGCTACC
AATGGCGAAATTTTCAATACCTATGGTCATAATCATCAATCAGCCACAGTCACTAAAATCACTGCTTCTAATGAA
AGCAGCAATGGTGTCTGTTATCTTTCAGAAACGGCTAACTTGGGGAAGTTAATATGCATTCCAATGGCACTAAGA
GCTGCGATGGAGCTAAATGTGTTCCAACTTATCTCAAAGTTCGGAACTGACGCAAAAGTTTCGGCTTCTGAAATT
GCCTCTAAAATGCCAAACGCGAAGAATAATCCTGAAGCAGCTATGTATTTGGATAGAATTCTTCGACTGCTCGGG
GCAAGTTCTATTCTTTCTGTTTCTACTACAAAAAAATCAATCAACAGAGGAGGAGATGATGTAGTAGTACATGAG
AAGCTTTATGGGTTAACAAATTCGTCGTGTTGTTTGGTCCCTCGACAAGAAGACGGGGTGTCATTAGTCGAAGAA
TTGCTATTCACATCTGACAAGGTTGTTGTGGATAGTTTTTTCAAACTGAAATGTGTGGTGGAAGAAAAAGACAGT
GTGCCATTTGAGGTTGCTCATGGTGCTAAAATCTTTGAGTATGCTGCTACAGAACCAAGAATGAATCAAGTATTT
AACGATGGAATGGCAGTTTTCTCTATTGTTGTTTTTGAGGCTGTTTTTAGAGTTTACGATGGATTTCTTGATATG
AAAGAATTGTTAGATGTTGGTGGTGGTATTGGTACTTCGGTTAGTAAGATTGTTGCTAAATACCCTTTGATTCGC
GGTGTCAACTTCGACTTGCCTCATGTTATTTCTGTTGCCCCTCAATACCCAGGTATACCTTCTTCTTCTTTTTTC
TGAAAAGAACGGGTTCGAATTTTTACAGAATTTTTTTTCTCATTCGATACTCAAGCAACTCTATTAAAGTATACT
GTGTAATAATGCATGCAGGTGTAGAGCATGTTGCAGGAGATATGTTCGAGGAAGTCCCAAAGGGTCAAAACATGT
TGCTAAAAGTAAGCTAACCATACTCAATTTTCTTAATAATTAGGAAAATTGCAAAAACCGTCACAATATTATAAA
GGCATCTGAAGTGCCATCACTCAGATACCGATGCTATGTACTCTATACATTGACAAAATTCCATGGTATCAAGTC
TCAACCTGCCGGTTATAATAATTTTTTTCAGGCTTTCTTTAAAAGAAATTATTTTGAATGGTAAAAATCATCATT
ATATTGGAGAAAAGTGCAGATCTTGCTACATTAAAATTTATAATATAATAAAACATTTGTTTATGGTTGTTTGAA
AAAAAAAATCTCATTGTTAATGCATCTTTCTAAGTTAATGGTGATTAATGGTGAATAATATGATATCTTATTACC
GTCTTGACACTTTTTTTTTTGTCGTAGACAAAATATTTCCAACTTTTCTATATTAATAAAATCAGAAATATTTCA
TTTATATGAATATTAAAATAAGAAGGTGCATGAGTAATATTCCAAATTTCTTAAAGCGTTTTTTATAGCAGTACG
GCGTTTTCTCAAATCTTATTAACCCATAATTAAAGGGTTTCCGTAAATTAAATTGAGGGATATCAAAACAAAAAC
AAAAAATAGGGTTATTTTGCAGTAAAATCAATAACCCCTTATCATATGAAAAGGATAACTTAGTCTACCCCAATT
TGGAGAGATATGGGCAATTATTGTATTACTAGTTCGTTTGAGCATTGATAATATTTTTCATTAGATTTATACTCA
ATAAAATATATGAACTATATTGATAAAGATTAATAATGCAGTGGGTACTGCACGATTGGGGTGATGAACGATGTG
TGAAGCTGTTAAAGAATTGTTGGAACTCATTACCTGTGGGTGGAAAAGTTTTGATAATCGAGTTTGTTCTCCCGA
ATGAACTTGGTAACAATGCTGAATCATTCAATGCGTTGATTCCCGATTTACTCCTGATGGCTCTGAATCCAGGCG
GTAAAGAGCGAACGATTTCCGAATACGATGATTTAGGCAAAGCAGCTGGATTCATAAAAACTATACCTATCCCTA
TCTCCAATGGTCTTCATGTCATTGAGTTTCACAAATGAATGGTTATTGAGTGCTTTGGTAATTAAACTACCAAGA
TAACTACATCCATTTCATGCATTTGCTTTTTTTTTTTCTTTTTTTTTCTTTTTTTTTCTTTTTGTTTTGTATTCCA
GGTGTGAACTAGTTAGTGTGTTGAGTGGACAAAAGTAAGTAATCGTATTTTGTGTT

Figure 3b

| Start | End | Feature |
|---|---|---|
| 1 | 74 | 5′ untranslated region |
| 75 | 851 | exon 1 |
| 852 | 938 | intron |
| 939 | 1232 | exon 2 |
| 1233 | 1440 | 3′ untranslated region |

GAATCAGAAACTTTCTTCTAAAATCTTTCAATACCAGTACTGTTAGTTTCCGATAAGAGCCACACTAA
TCCATTATGGAAATTCATTTAGAAAGCCAAGAACAAGAAATGAAATATCAATCTCAAATCTGGAACCA
AATATGTGGCACTGTTGATACCTCTGTTCTGAGATGTGCAATTCAATTAGGTATATTTGATGCCATTC
ATAACTCTGGCAAACCAATGATTACCTTAACCGAATTATCAAGCATTGTTTCATCACCCTCTTCATCT
TCAATCGAACCCTGCAACTTGTATAGATTAGTGAGATACTTATCCCAAATGGATCTCATTAGTATCGG
AGAATGTTTGAATGAAGCAACTGTTTCATTAACAGGCACATCCAAGTTACTACTTAGAAACCAAGAAA
AGAGTTTAATTGATTGGGTATTGGCAATTTCTTGCGAAATGATGGTTGTTGTTTGGCACGAACTAAGT
AGCTCTGTTTCAACTCCTGCGGATGAGCCTCCAATCTTCCAGAAGGTTCATGGTAAAAATGCTTTAGA
ATTAGCAGGGGAATTTCCAGAATGGAATGATCTGATCAACAATGCTATGACTAGTGATACTAGTGTAA
CTAAGCCAGCGCTAATACAAGGATGTGGCAAAATCCTGAACGGAGTTACATCGTTAATTGATGTCGGT
GGTGGTCACGGTGCCACTATGGCCTACATAGTTGAAGCTTTTCCTCACATAAAAGGTGCGGTAATCGA
TTTACCACATGTTGTTGAAGCCGCTCCGGAGCGTCCAGGTGTTGAGTTCATCAGCGGTGATATATTCA
AGTCCATTTCTAACGCTGATGCTGTGTTGTTGAAGGTATGTAAAGAGTAGCTAACCTTAGTGCGTCTA
ATTTATTCCACAAATTTTTCTGATGCATTTTATTCTTATTTTTGGTTTTTGCAGTATGTCCTGCACAA
TTGGGAAGATACGGAATGTGTGAATTTACTGAAGAGATGTAAGGAAGCAGTTCCGGCAGACAAAGGAA
AAGTGATCATAATGGATTTAGTAATAGACGACGATGATAACAGTATTTTAACGCAGGCAAAGTTGAGC
CTTGATCTCACTGTGATGAACCATGGAGGAGGTAGAGAAAGGACTAAAGAAGATTGGAGAAATCTAAT
TGAGATGTCTGGATTTAGTAGGCATGAAATAATTCCAATATCTGCCATGCCATCAATTATTGTTGCTT
ATCCTTAGTTAAGTCACCCGCATGTTTACTTGAACGGGAATAAGTTGGGGGCGTGTTGAATCTGTTAA
CATCGCAATTGTGCCTTTACTTTATGCATTCTCATTCCGGTAGAAACTGTTTGGGGCATTCGGATTCT
GCTGAGCCCTTTTATGTATGTTTGTTTGTTGGTTGGTTGGTTTTCAAGTAACTGAAGTTTCTTCTCTG
TTTTCAAGGCAT

Figure 3c

| Start | End | Feature |
|---|---|---|
| 1 | 120 | 5′ untranslated region |
| 121 | 846 | exon 1 |
| 847 | 994 | intron |
| 995 | 1288 | exon 2 |
| 1289 | 1436 | 3′ untranslated region |

```
AAGTTGCAGGTAGGGTTATGAGCAAGCTCAATTATCTCTCCTATAAAAGCTAACATTAGAAAAACTAA
TAAGCACACAAACCGTAAAAGTTCTGAAGATAGACAAAACAAGAGAAAAAAGATGGAAGTAGTAAGTA
AGATTGATCAAGAAAACCAAGCAAAAATTTGGAAACAAATTTTTGGTTTTGCAGAATCATTAGTTCTA
AAATGTGCAGTTCAGTTAGAGATTGCTGAAACACTTCATAATAATGTAAAACCCATGTCTTTATCCGA
GTTAGCATCTAAACTTCCGGCTCAACCCGTTAATGAAGACCGTTTGTACCGAATTCTGCATTTCTTAG
TTCACATGAAACTCTTCAACAAAGATGCTACCACACAGAAATATTCATTAGCTCCACCAGCAAAGTAT
TTGCTAAAAGGCTGGGAAAAATCAATGGTTCCTTCAATATTAAGCGTGACTGATAAAGATTTTACAGC
TCCATGGAATCATCTTGGGGACGGTTTAACCGGTAACTGTAACGCTTTTGAGAAAGCGTTAGGAAAGG
GCATTCGGGTTTATATGAGAGAAAATCCTGAAAAAGATCAATTGTTTAATGAAGGAATGGCTTGTGAT
ACTAGATTATTTGCTTCAGCATTGGTTAACGAGTGCAAAAGTATTTTCAGTGACGGGATCAATACACT
TGCCGGTGTTGGCCGTGGTACTGGTACTGCAGTGAAAGCCATATCCAAAGCTTTTCCGGATATTAAGT
GCACAATCCATGATCTTCCTGAAGTTACCAGTAAAAATAGTAAAATTCCAAGAGATGTTTTTAAGTCC
GTTCCTAGTGCAGACGCCATCTTTATGAAGGTAACTTCTAAGAAATTTTGTTTTAGAATATTCGTTGC
AACTCTAATTGACAACATTCATAAAAAAATATGTTAATGGTCTTAATTTATTAATTCTAGTAGAGTTAC
TTAAATGATATACAAAAATTCAAAATCATATAACATTTGCAGAGCATTCTTCACGAATGGAACGATGA
GGAATGTATTCAAATCTTGAAACGATGCAAAGAAGCAATACCAAAAGGGGGCAAAGTTATCATTGCGG
ATGTCGTAATAGACATGGACTCGACTCATCCGTATTCAAAATCTAGACTCGCAATGGATTTGGCTATG
ATGCTCCACACGGGTGGAAAAGAGAGAACTGAAGAAGATTGGAAAAAACTTATTGATGCTGCAGGTTT
TGCTAGCTGTAAAATTACTAAACTATCTGCTCTCCAGTCTGTTATTGAGGCTTACCCTCATTGAGGAT
AATTTTTATCCTTCTGTTTTCCCTTTGGTTAATTGTTGCCTTCTCTTTGGATCATGGTTGCGTTTATA
ATAAATGCAGCGTTTCTTTCCTGGCGGTAAGTGCAAGAAAGAAAAAGCTTCCAGAAACTTCCTTGAGT
ATGCCTGG
```

Figure 4a

MATNGEIFNTYGHNHQSATVTKITASNESSNGVCYLSETANLGKLICIPMALRAAMELNVFQLISKFGTDAKVSA
SEIASKMPNAKNNPEAAMYLDRILRLLGASSILSVSTTKKSINRGGDDVVVHEKLYGLTNSSCCLVPRQEDGVSL
VEELLFTSDKVVVDSFFKLKCVVEEKDSVPFEVAHGAKIFEYAATEPRMNQVFNDGMAVFSIVVFEAVFRVYDGF
LDMKELLDVGGGIGTSVSKIVAKYPLIRGVNFDLPHVISVAPQYPGVEHVAGDMFEEVPKGQNMLLKWVLHDWGD
ERCVKLLKNCWNSLPVGGKVLIIEFVLPNELGNNAESFNALIPDLLLMALNPGGKERTISEYDDLGKAAGFIKTI
PIPISNGLHVIEFHK.

Figure 4b

MEIHLESQEQEMKYQSQIWNQICGTVDTSVLRCAIQLGIFDAIHNSGKPMITLTELSSIVSSPSSSSIEPCNLYR
LVRYLSQMDLISIGECLNEATVSLTGTSKLLLRNQEKSLIDWVLAISCEMMVVVWHELSSSVSTPADEPPIFQKV
HGKNALELAGEFPEWNDLINNAMTSDTSVTKPALIQGCGKILNGVTSLIDVGGGHGATMAYIVEAFPHIKGAVID
LPHVVEAAPERPGVEFISGDIFKSISNADAVLLKYVLHNWEDTECVNLLKRCKEAVPADKGKVIIMDLVIDDDDN
SILTQAKLSLDLTVMNHGGGRERTKEDWRNLIEMSGFSRHEIIPISAMPSIIVAYP

Figure 4c

MEVVSKIDQENQAKIWKQIFGFAESLVLKCAVQLEIAETLHNNVKPMSLSELASKLPAQPVNEDRLYRILHFLVH
MKLFNKDATTQKYSLAPPAKYLLKGWEKSMVPSILSVTDKDFTAPWNHLGDGLTGNCNAFEKALGKGIRVYMREN
PEKDQLFNEGMACDTRLFASALVNECKSIFSDGINTLAGVGRGTGTAVKAISKAFPDIKCTIHDLPEVTSKNSKI
PRDVFKSVPSADAIFMKSILHEWNDEECIQILKRCKEAIPKGGKVIIADVVIDMDSTHPYSKSRLAMDLAMMLHT
GGKERTEEDWKKLIDAAGFASCKITKLSALQSVIEAYPH

Figure 5

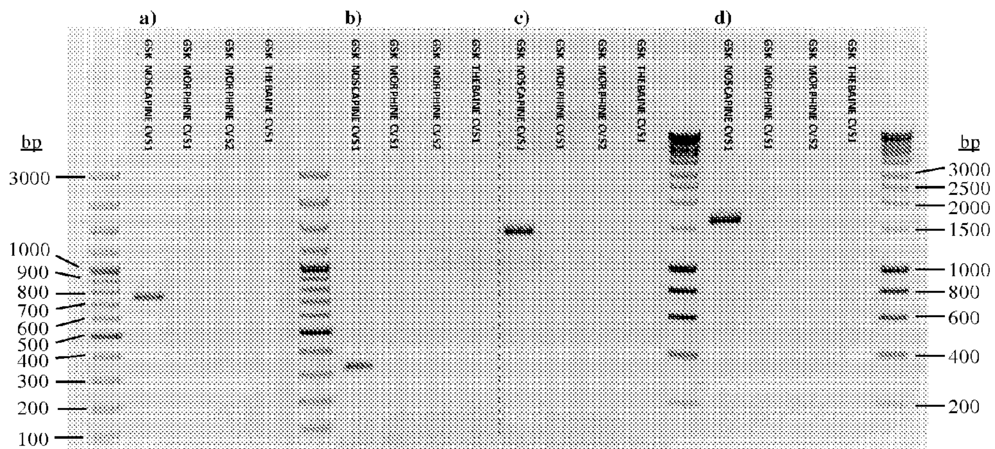

Figure 6a

| F2: GSK THEBAINE CVS1 x GSK NOSCAPINE CVS | | | | |
|---|---|---|---|---|
| SUM | Noscapine + | | Noscapine - | |
| 276 | 61 | | 215 | |
| | *PSMT1* + | *PSMT1* - | *PSMT1* + | *PSMT1* - |
| | 61 | 0 | 131 | 84 |
| SUM | *PSMT1* + | | *PSMT1* - | |
| 276 | 192 | | 84 | |
| | Noscapine + | Noscapine - | Noscapine + | Noscapine - |
| | 61 | 131 | 0 | 84 |

Figure 6b

| F2: GSK THEBAINE CVS1 x GSK NOSCAPINE CVS | | | | |
|---|---|---|---|---|
| SUM | Noscapine + | | Noscapine - | |
| 276 | 61 | | 215 | |
| | *PSMT2* + | *PSMT2* - | *PSMT2* + | *PSMT2* - |
| | 59* | 0 | 127** | 84 |
| SUM | *PSMT2* + | | *PSMT2* - | |
| 276 | 186*** | | 84 | |
| | Noscapine + | Noscapine - | Noscapine + | Noscapine - |
| | 61 | 131 | 0 | 84 |

* two genotyping assays failed; four genotyping assays failed; *in total the *PSMT2* genotyping assay failed on DNA samples from six F2 plants that were positive for *PSMT1* and *PSMT3* (Figure 6a and 6c)

Figure 6c

| F2: GSK THEBAINE CVS1 x GSK NOSCAPINE CVS | | | | |
|---|---|---|---|---|
| SUM | Noscapine + | | Noscapine - | |
| 276 | 61 | | 215 | |
| | *PSMT3* + | *PSMT3* - | *PSMT3* + | *PSMT3* - |
| | 61 | 0 | 131 | 84 |
| SUM | *PSMT3* + | | *PSMT3* - | |
| 276 | 192 | | 84 | |
| | Noscapine + | Noscapine - | Noscapine + | Noscapine - |
| | 61 | 131 | 0 | 84 |

Figure 11

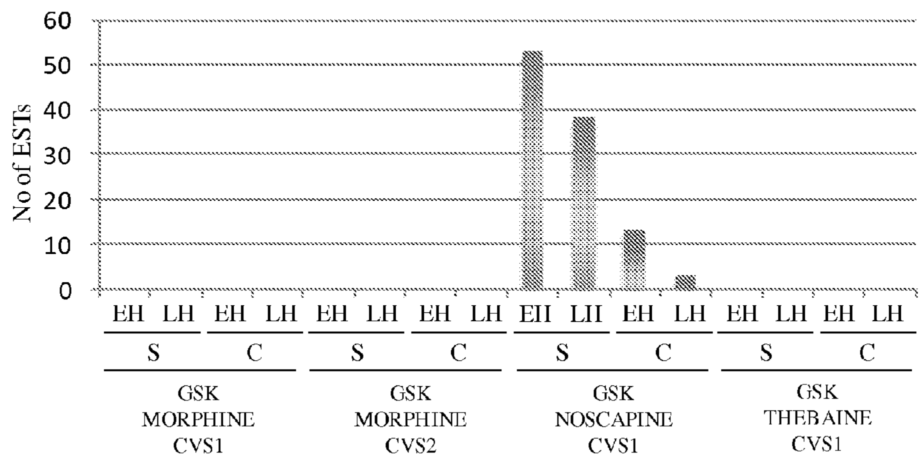

Figure 12

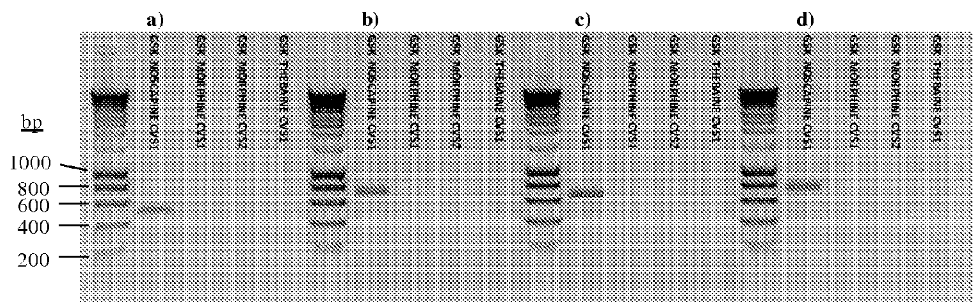

Figure 13

GAGGTGTTCATTGCCATGTCAAAGGCATTAAACTTCATAAACCCAGATGAGCTTTCGATGCAGTGCATTTTGATA
GCTTTGAACCGTTTCCTTCAGGAAAAGCATGGTTCCAAGATGGCCTTTTTAGATGGTAATCCTCCCGAGAGACTT
TGCAAGCCGGTCGTGGATCATATAGAGTCACTTGGCGGTGAAGTCCGTCTCAATTCCAGGATTAAAAAGATTGAG
CTTAAAAAAGATGGTACTGTGAAACGTCTAATGCTCACCAACGGTGATGCAATAGAAGGAGATGCTTATGTCATT
GCAACCCCAGTGGACATCCTAAAGCTGCTTATACCCGAGGAGTGGAAAGAAGTTGGGTACTTTAAAAGATTGGAT
AAATTAGTTGGAGTTCCTGTGATTAACGTCCATATATGGTTTGACAGGAAATTGAAAAATACATATGATCATCTT
CTCTTCAGCAGAAGTCCCCTCTTAAGCGTATACGCTGACATGTCAGTGACATGCAAGGAATATTATGACCCAAAC
AAATCCATGCTTGAGTTGGTATTTGCACCCGCTGAGGAATGGATCTCGCGCAGTGACTCTGAAATTATTGAAGCT
ACTATGCAGGAGCTTGCGAAAC

Figure 14

TGGTCATAATCATCAATCAGCCACAGTCACTAAAATCACTGCTTCTAATGAAAGCAGCAATGGTGTCTGTTATCT
TTCAGAAACGGCTAACTTGGGGAAGTTAATATGCATTCCAATGGCACTAAGAGCTGCGATGGAGCTAAATGTGTT
CCAACTTATCTCAAAGTTCGGAACTGACGCAAAAGTTTCGGCTTCTGAAATTGCCTCTAAAATGCCAAACGCGAA
GAATAATCCTGAAGCAGCTATGTATTTGGATAGAATTCTTCGACTGCTCGGGGCAAGTTCTATTCTTTCTGTTTC
TACTACAAAAAAATCAATCAACAGAGGAGGAGATGATGTAGTAGTACATG

GTGTAACTAAGCCAGCGCTAATACAAGGATGTGGCAAAATCCTGAACGGAGTTACATCGTTAATTGATGTCGGTG
GTGGTCACGGTGCCACTATGGCCTACATAGTTGAAGCTTTTCCTCACATAAAAGGTGCGGTAATCGATTTACCAC
ATGTTGTTGAAGCCGCTCCGGAGCGTCCAGGTGTTGAGTTCATCAGCGGTGATATATTCAAGT

SEQUENCE LISTING

<160> NUMBER OF SEQ ID NOS: 57

<210> SEQ ID NO 1
<211> LENGTH: 1173
<212> TYPE: DNA
<213> ORGANISM: Papaver somniferum

<400> SEQUENCE: 1

```
atggctacca atggcgaaat tttcaatacc tatggtcata atcatcaatc agccacagtc     60
actaaaatca ctgcttctaa tgaaagcagc aatggtgtct gttatctttc agaaacggct    120
aacttgggga agttaatatg cattccaatg gcactaagag ctgcgatgga gctaaatgtg    180
ttccaactta tctcaaagtt cggaactgac gcaaaagttt cggcttctga aattgcctct    240
aaaatgccaa acgcgaagaa taatcctgaa gcagctatgt atttggatag aattcttcga    300
ctgctcgggg caagttctat tctttctgtt tctactacaa aaaaatcaat caacagagga    360
ggagatgatg tagtagtaca tgagaagctt tatgggttaa caaattcgtc gtgttgtttg    420
gtccctcgac aagaagacgg ggtgtcatta gtcgaagaat tgctattcac atctgacaag    480
gttgttgtgg atagtttttt caaactgaaa tgtgtggtgg aagaaaaaga cagtgtgcca    540
tttgaggttg ctcatggtgc taaaatcttt gagtatgctg ctacagaacc aagaatgaat    600
caagtattta acgatggaat ggcagttttc tctattgttg tttttgaggc tgtttttaga    660
gtttacgatg gatttcttga tatgaaagaa ttgttagatg ttggtggtgg tattggtact    720
tcggttagta agattgttgc taaataccct ttgattcgcg gtgtcaactt cgacttgcct    780
catgttattt ctgttgcccc tcaataccca ggtgtagagc atgttgcagg agatatgttc    840
gaggaagtcc caaagggtca aaacatgttg ctaaaatggg tactgcacga ttggggtgat    900
gaacgatgtg tgaagctgtt aaagaattgt tggaactcat tacctgtggg tggaaaagtt    960
ttgataatcg agtttgttct cccgaatgaa cttggtaaca atgctgaatc attcaatgcg   1020
ttgattcccg atttactcct gatggctctg aatccaggcg gtaaagagcg aacgatttcc   1080
gaatacgatg atttaggcaa agcagctgga ttcataaaaa ctatacctat ccctatctcc   1140
aatggtcttc atgtcattga gtttcacaaa tga                                1173
```

<210> SEQ ID NO 2
<211> LENGTH: 1071
<212> TYPE: DNA
<213> ORGANISM: Papaver somniferum

<400> SEQUENCE: 2

```
atggaaattc atttagaaag ccaagaacaa gaaatgaaat atcaatctca aatctggaac     60
caaatatgtg gcactgttga tacctctgtt ctgagatgtg caattcaatt aggtatattt    120
gatgccattc ataactctgg caaaccaatg attaccttaa ccgaattatc aagcattgtt    180
tcatcaccct cttcatcttc aatcgaaccc tgcaacttgt atagattagt gagatactta    240
tcccaaatgg atctcattag tatcggagaa tgtttgaatg aagcaactgt ttcattaaca    300
ggcacatcca agttactact tagaaaccaa gaaaagagtt taattgattg ggtattggca    360
atttcttgcg aaatgatggt tgttgtttgg cacgaactaa gtagctctgt ttcaactcct    420
gcggatgagc ctccaatctt ccagaaggtt catggtaaaa atgctttaga attagcaggg    480
gaatttccag aatggaatga tctgatcaac aatgctatga ctagtgatac tagtgtaact    540
aagccagcgc taatacaagg atgtggcaaa atcctgaacg gagttacatc gttaattgat    600
gtcggtggtg gtcacggtgc cactatggcc tacatagttg aagcttttcc tcacataaaa    660
```

ggtgcggtaa tcgatttacc acatgttgtt gaagccgctc cggagcgtcc aggtgttgag 720
ttcatcagcg gtgatatatt caagtccatt tctaacgctg atgctgtgtt gttgaagtat 780
gtcctgcaca attgggaaga tacggaatgt gtgaatttac tgaagagatg taaggaagca 840
gttccggcag acaaaggaaa agtgatcata atggatttag taatagacga cgatgataac 900
agtattttaa cgcaggcaaa gttgagcctt gatctcactg tgatgaacca tggaggaggt 960
agagaaagga ctaaagaaga ttggagaaat ctaattgaga tgtctggatt tagtaggcat 1020
gaaataattc caatatctgc catgccatca attattgttg cttatcctta g 1071

<210> SEQ ID NO 3
<211> LENGTH: 1020
<212> TYPE: DNA
<213> ORGANISM: Papaver somniferum

<400> SEQUENCE: 3
atggaagtag taagtaagat tgatcaagaa aaccaagcaa aaatttggaa acaaattttt 60
ggttttgcag aatcattagt tctaaaatgt gcagttcagt tagagattgc tgaaacactt 120
cataataatg taaaacccat gtctttatcc gagttagcat ctaaacttcc ggctcaaccc 180
gttaatgaag accgtttgta ccgaattctg catttcttag ttcacatgaa actcttcaac 240
aaagatgcta ccacacagaa atattcatta gctccaccag caaagtattt gctaaaaggc 300
tgggaaaaat caatggttcc ttcaatatta agcgtgactg ataaagattt tacagctcca 360
tggaatcatc ttggggacgg tttaaccggt aactgtaacg cttttgagaa agcgttagga 420
aagggcattc gggtttatat gagagaaaat cctgaaaaag atcaattgtt taatgaagga 480
atggcttgtg atactagatt atttgcttca gcattggtta acgagtgcaa aagtattttc 540
agtgacggga tcaatacact tgccggtgtt ggccgtggta ctggtactgc agtgaaagcc 600
atatccaaag cttttccgga tattaagtgc acaatccatg atcttcctga agttaccagt 660
aaaaatagta aaattccaag agatgttttt aagtccgttc ctagtgcaga cgccatcttt 720
atgaagagca ttcttcacga atggaacgat gaggaatgta ttcaaatctt gaaacgatgc 780
aaagaagcaa taccaaaagg gggcaaagtt atcattgcgg atgtcgtaat agacatggac 840
tcgactcatc cgtattcaaa atctagactc gcaatggatt tggctatgat gctccacacg 900
ggtggaaaag agagaactga agaagattgg aaaaaactta ttgatgctgc aggttttgct 960
agctgtaaaa ttactaaact atctgctctc cagtctgtta ttgaggctta ccctcattga 1020

<210> SEQ ID NO 4
<211> LENGTH: 2306
<212> TYPE: DNA
<213> ORGANISM: Papaver somniferum

<400> SEQUENCE: 4
cacaccaaac ttgatcattg tcataaaaaa cagtcctaat tgtcatcaat caaaaacagt 60
cctaacatgg ctaccaatgg cgaaattttc aatacctatg gtcataatca tcaatcagcc 120
acagtcacta aaatcactgc ttctaatgaa agcagcaatg gtgtctgtta tctttcagaa 180
acggctaact tggggaagtt aatatgcatt ccaatggcac taagagctgc gatggagcta 240
aatgtgttcc aacttatctc aaagttcgga actgacgcaa aagtttcggc ttctgaaatt 300
gcctctaaaa tgccaaacgc gaagaataat cctgaagcag ctatgtattt ggatagaatt 360
cttcgactgc tcggggcaag ttctattctt tctgtttcta ctacaaaaaa atcaatcaac 420

```
agaggaggag atgatgtagt agtacatgag aagctttatg ggttaacaaa ttcgtcgtgt    480

tgtttggtcc ctcgacaaga agacggggtg tcattagtcg aagaattgct attcacatct    540

gacaaggttg ttgtggatag ttttttcaaa ctgaaatgtg tggtggaaga aaaagacagt    600

gtgccatttg aggttgctca tggtgctaaa atctttgagt atgctgctac agaaccaaga    660

atgaatcaag tatttaacga tggaatggca gttttctcta ttgttgtttt tgaggctgtt    720

tttagagttt acgatggatt tcttgatatg aaagaattgt tagatgttgg tggtggtatt    780

ggtacttcgg ttagtaagat tgttgctaaa taccctttga ttcgcggtgt caacttcgac    840

ttgcctcatg ttatttctgt tgcccctcaa tacccaggta taccttcttc ttcttttttc    900

tgaaaagaac gggttcgaat ttttacagaa tttttttttct cattcgatac tcaagcaact    960

ctattaaagt atactgtgta ataatgcatg caggtgtaga gcatgttgca ggagatatgt   1020

tcgaggaagt cccaaagggt caaaacatgt tgctaaaagt aagctaacca tactcaattt   1080

tcttaataat taggaaaatt gcaaaaaccg tcacaatatt ataaaggcat ctgaagtgcc   1140

atcactcaga taccgatgct atgtactcta tacattgaca aaattccatg gtatcaagtc   1200

tcaacctgcc ggttataata atttttttca ggctttcttt aaaagaaatt attttgaatg   1260

gtaaaaatca tcattatatt ggagaaaagt gcagatcttg ctacattaaa atttataata   1320

taataaaaca tttgtttatg gttgtttgaa aaaaaaaatc tcattgttaa tgcatctttc   1380

taagttaatg gtgattaatg gtgaataata tgatatctta ttaccgtctt gacacttttt   1440

tttttgtcgt agacaaaata tttccaactt ttctatatta ataaaatcag aaatatttca   1500

tttatatgaa tattaaaata agaaggtgca tgagtaatat tccaaatttc ttaaagcgtt   1560

ttttatagca gtacggcgtt ttctcaaatc ttattaaccc ataattaaag ggtttccgta   1620

aattaaattg agggatatca aaacaaaaac aaaaaatagg gttattttgc agtaaaatca   1680

ataacccctt atcatatgaa aaggataact tagtctaccc caatttggag agatatgggc   1740

aattattgta ttactagttc gtttgagcat tgataatatt tttcattaga tttatactca   1800

ataaaatata tgaactatat tgataaagat taataatgca gtgggtactg cacgattggg   1860

gtgatgaacg atgtgtgaag ctgttaaaga attgttggaa ctcattacct gtgggtggaa   1920

aagttttgat aatcgagttt gttctcccga atgaacttgg taacaatgct gaatcattca   1980

atgcgttgat tcccgattta ctcctgatgg ctctgaatcc aggcggtaaa gagcgaacga   2040

tttccgaata cgatgattta ggcaaagcag ctggattcat aaaaactata cctatcccta   2100

tctccaatgg tcttcatgtc attgagtttc acaaatgaat ggttattgag tgctttggta   2160

attaaactac caagataact acatccattt catgcatttg cttttttttt ttcttttttt   2220

tctttttttt tctttttgtt ttgtattcca ggtgtgaact agttagtgtg ttgagtggac   2280

aaaagtaagt aatcgtattt tgtgtt                                        2306
```

<210> SEQ ID NO 5
<211> LENGTH: 1440
<212> TYPE: DNA
<213> ORGANISM: Papaver somniferum

<400> SEQUENCE: 5

```
gaatcagaaa ctttcttcta aaatctttca ataccagtac tgttagtttc cgataagagc     60

cacactaatc cattatggaa attcatttag aaagccaaga acaagaaatg aaatatcaat    120

ctcaaatctg gaaccaaata tgtggcactg ttgatacctc tgttctgaga tgtgcaattc    180

aattaggtat atttgatgcc attcataact ctggcaaacc aatgattacc ttaaccgaat    240
```

```
tatcaagcat tgtttcatca ccctcttcat cttcaatcga accctgcaac ttgtatagat    300
tagtgagata cttatcccaa atggatctca ttagtatcgg agaatgtttg aatgaagcaa    360
ctgtttcatt aacaggcaca tccaagttac tacttagaaa ccaagaaaag agtttaattg    420
attgggtatt ggcaatttct tgcgaaatga tggttgttgt ttggcacgaa ctaagtagct    480
ctgtttcaac tcctgcggat gagcctccaa tcttccagaa ggttcatggt aaaaatgctt    540
tagaattagc aggggaattt ccagaatgga atgatctgat caacaatgct atgactagtg    600
atactagtgt aactaagcca gcgctaatac aaggatgtgg caaaatcctg aacggagtta    660
catcgttaat tgatgtcggt ggtggtcacg gtgccactat ggcctacata gttgaagctt    720
ttcctcacat aaaaggtgcg gtaatcgatt taccacatgt tgttgaagcc gctccggagc    780
gtccaggtgt tgagttcatc agcggtgata tattcaagtc catttctaac gctgatgctg    840
tgttgttgaa ggtatgtaaa gagtagctaa ccttagtgcg tctaatttat tccacaaatt    900
tttctgatgc attttattct tatttttggt ttttgcagta tgtcctgcac aattgggaag    960
atacggaatg tgtgaattta ctgaagagat gtaaggaagc agttccggca gacaaaggaa   1020
aagtgatcat aatggattta gtaatagacg acgatgataa cagtatttta acgcaggcaa   1080
agttgagcct tgatctcact gtgatgaacc atggaggagg tagagaaagg actaaagaag   1140
attggagaaa tctaattgag atgtctggat ttagtaggca tgaaataatt ccaatatctg   1200
ccatgccatc aattattgtt gcttatcctt agttaagtca cccgcatgtt tacttgaacg   1260
ggaataagtt gggggcgtgt tgaatctgtt aacatcgcaa ttgtgccttt actttatgca   1320
ttctcattcc ggtagaaact gtttggggca ttcggattct gctgagccct tttatgtatg   1380
tttgtttgtt ggttggttgg ttttcaagta actgaagttt cttctctgtt ttcaaggcat   1440
```

<210> SEQ ID NO 6
<211> LENGTH: 1436
<212> TYPE: DNA
<213> ORGANISM: Papaver somniferum

<400> SEQUENCE: 6

```
aagttgcagg tagggttatg agcaagctca attatctctc ctataaaagc taacattaga     60
aaaactaata agcacacaaa ccgtaaaagt tctgaagata gacaaaacaa gagaaaaaag    120
atggaagtag taagtaagat tgatcaagaa aaccaagcaa aaatttggaa acaaattttt    180
ggttttgcag aatcattagt tctaaaatgt gcagttcagt tagagattgc tgaaacactt    240
cataataatg taaaacccat gtctttatcc gagttagcat ctaaacttcc ggctcaaccc    300
gttaatgaag accgtttgta ccgaattctg catttcttag ttcacatgaa actcttcaac    360
aaagatgcta ccacacagaa atattcatta gctccaccag caaagtattt gctaaaaggc    420
tgggaaaaat caatggttcc ttcaatatta agcgtgactg ataaagattt tacagctcca    480
tggaatcatc ttggggacgg tttaaccggt aactgtaacg cttttgagaa agcgttagga    540
aagggcattc gggtttatat gagagaaaat cctgaaaaag atcaattgtt taatgaagga    600
atggcttgtg atactagatt atttgcttca gcattggtta acgagtgcaa aagtattttc    660
agtgacggga tcaatacact tgccggtgtt ggccgtggta ctggtactgc agtgaaagcc    720
atatccaaag cttttccgga tattaagtgc acaatccatg atcttcctga agttaccagt    780
aaaaatagta aaattccaag agatgttttt aagtccgttc ctagtgcaga cgccatcttt    840
atgaaggtaa cttctaagaa attttgtttt agaatattcg ttgcaactct aattgacaac    900
```

```
attcataaaa aatatgttaa tggtcttaat ttattaattc tagtagagtt acttaaatga    960

tatacaaaaa ttcaaaatca tataacattt gcagagcatt cttcacgaat ggaacgatga   1020

ggaatgtatt caaatcttga aacgatgcaa agaagcaata ccaaaagggg gcaaagttat   1080

cattgcggat gtcgtaatag acatggactc gactcatccg tattcaaaat ctagactcgc   1140

aatggatttg gctatgatgc tccacacggg tggaaaagag agaactgaag aagattggaa   1200

aaaacttatt gatgctgcag gttttgctag ctgtaaaatt actaaactat ctgctctcca   1260

gtctgttatt gaggcttacc ctcattgagg ataattttta tccttctgtt ttccctttgg   1320

ttaattgttg ccttctcttt ggatcatggt tgcgtttata ataaatgcag cgtttctttc   1380

ctggcggtaa gtgcaagaaa gaaaaagctt ccagaaactt ccttgagtat gcctgg        1436


<210> SEQ ID NO 7
<211> LENGTH: 390
<212> TYPE: PRT
<213> ORGANISM: Papaver somniferum

<400> SEQUENCE: 7

Met Ala Thr Asn Gly Glu Ile Phe Asn Thr Tyr Gly His Asn His Gln
1               5                   10                  15

Ser Ala Thr Val Thr Lys Ile Thr Ala Ser Asn Glu Ser Ser Asn Gly
            20                  25                  30

Val Cys Tyr Leu Ser Glu Thr Ala Asn Leu Gly Lys Leu Ile Cys Ile
        35                  40                  45

Pro Met Ala Leu Arg Ala Ala Met Glu Leu Asn Val Phe Gln Leu Ile
    50                  55                  60

Ser Lys Phe Gly Thr Asp Ala Lys Val Ser Ala Ser Glu Ile Ala Ser
65                  70                  75                  80

Lys Met Pro Asn Ala Lys Asn Asn Pro Glu Ala Ala Met Tyr Leu Asp
                85                  90                  95

Arg Ile Leu Arg Leu Leu Gly Ala Ser Ser Ile Leu Ser Val Ser Thr
            100                 105                 110

Thr Lys Lys Ser Ile Asn Arg Gly Gly Asp Asp Val Val Val His Glu
        115                 120                 125

Lys Leu Tyr Gly Leu Thr Asn Ser Ser Cys Cys Leu Val Pro Arg Gln
    130                 135                 140

Glu Asp Gly Val Ser Leu Val Glu Glu Leu Leu Phe Thr Ser Asp Lys
145                 150                 155                 160

Val Val Val Asp Ser Phe Phe Lys Leu Lys Cys Val Val Glu Glu Lys
                165                 170                 175

Asp Ser Val Pro Phe Glu Val Ala His Gly Ala Lys Ile Phe Glu Tyr
            180                 185                 190

Ala Ala Thr Glu Pro Arg Met Asn Gln Val Phe Asn Asp Gly Met Ala
        195                 200                 205

Val Phe Ser Ile Val Val Phe Glu Ala Val Phe Arg Val Tyr Asp Gly
    210                 215                 220

Phe Leu Asp Met Lys Glu Leu Leu Asp Val Gly Gly Gly Ile Gly Thr
225                 230                 235                 240

Ser Val Ser Lys Ile Val Ala Lys Tyr Pro Leu Ile Arg Gly Val Asn
                245                 250                 255

Phe Asp Leu Pro His Val Ile Ser Val Ala Pro Gln Tyr Pro Gly Val
            260                 265                 270

Glu His Val Ala Gly Asp Met Phe Glu Glu Val Pro Lys Gly Gln Asn
        275                 280                 285
```

```
Met Leu Leu Lys Trp Val Leu His Asp Trp Gly Asp Glu Arg Cys Val
    290                 295                 300

Lys Leu Leu Lys Asn Cys Trp Asn Ser Leu Pro Val Gly Gly Lys Val
305                 310                 315                 320

Leu Ile Ile Glu Phe Val Leu Pro Asn Glu Leu Gly Asn Asn Ala Glu
                325                 330                 335

Ser Phe Asn Ala Leu Ile Pro Asp Leu Leu Leu Met Ala Leu Asn Pro
            340                 345                 350

Gly Gly Lys Glu Arg Thr Ile Ser Glu Tyr Asp Asp Leu Gly Lys Ala
        355                 360                 365

Ala Gly Phe Ile Lys Thr Ile Pro Ile Pro Ile Ser Asn Gly Leu His
    370                 375                 380

Val Ile Glu Phe His Lys
385                 390


<210> SEQ ID NO 8
<211> LENGTH: 356
<212> TYPE: PRT
<213> ORGANISM: Papaver somniferum

<400> SEQUENCE: 8

Met Glu Ile His Leu Glu Ser Gln Glu Gln Glu Met Lys Tyr Gln Ser
1               5                   10                  15

Gln Ile Trp Asn Gln Ile Cys Gly Thr Val Asp Thr Ser Val Leu Arg
            20                  25                  30

Cys Ala Ile Gln Leu Gly Ile Phe Asp Ala Ile His Asn Ser Gly Lys
        35                  40                  45

Pro Met Ile Thr Leu Thr Glu Leu Ser Ser Ile Val Ser Ser Pro Ser
    50                  55                  60

Ser Ser Ser Ile Glu Pro Cys Asn Leu Tyr Arg Leu Val Arg Tyr Leu
65                  70                  75                  80

Ser Gln Met Asp Leu Ile Ser Ile Gly Glu Cys Leu Asn Glu Ala Thr
                85                  90                  95

Val Ser Leu Thr Gly Thr Ser Lys Leu Leu Leu Arg Asn Gln Glu Lys
            100                 105                 110

Ser Leu Ile Asp Trp Val Leu Ala Ile Ser Cys Glu Met Met Val Val
        115                 120                 125

Val Trp His Glu Leu Ser Ser Ser Val Ser Thr Pro Ala Asp Glu Pro
    130                 135                 140

Pro Ile Phe Gln Lys Val His Gly Lys Asn Ala Leu Glu Leu Ala Gly
145                 150                 155                 160

Glu Phe Pro Glu Trp Asn Asp Leu Ile Asn Asn Ala Met Thr Ser Asp
                165                 170                 175

Thr Ser Val Thr Lys Pro Ala Leu Ile Gln Gly Cys Gly Lys Ile Leu
            180                 185                 190

Asn Gly Val Thr Ser Leu Ile Asp Val Gly Gly Gly His Gly Ala Thr
        195                 200                 205

Met Ala Tyr Ile Val Glu Ala Phe Pro His Ile Lys Gly Ala Val Ile
    210                 215                 220

Asp Leu Pro His Val Val Glu Ala Ala Pro Glu Arg Pro Gly Val Glu
225                 230                 235                 240

Phe Ile Ser Gly Asp Ile Phe Lys Ser Ile Ser Asn Ala Asp Ala Val
                245                 250                 255

Leu Leu Lys Tyr Val Leu His Asn Trp Glu Asp Thr Glu Cys Val Asn
```

```
            260                 265                 270

Leu Leu Lys Arg Cys Lys Glu Ala Val Pro Ala Asp Lys Gly Lys Val
        275                 280                 285

Ile Ile Met Asp Leu Val Ile Asp Asp Asp Asp Asn Ser Ile Leu Thr
    290                 295                 300

Gln Ala Lys Leu Ser Leu Asp Leu Thr Val Met Asn His Gly Gly Gly
305                 310                 315                 320

Arg Glu Arg Thr Lys Glu Asp Trp Arg Asn Leu Ile Glu Met Ser Gly
                325                 330                 335

Phe Ser Arg His Glu Ile Ile Pro Ile Ser Ala Met Pro Ser Ile Ile
            340                 345                 350

Val Ala Tyr Pro
        355


<210> SEQ ID NO 9
<211> LENGTH: 339
<212> TYPE: PRT
<213> ORGANISM: Papaver somniferum

<400> SEQUENCE: 9

Met Glu Val Val Ser Lys Ile Asp Gln Glu Asn Gln Ala Lys Ile Trp
1               5                   10                  15

Lys Gln Ile Phe Gly Phe Ala Glu Ser Leu Val Leu Lys Cys Ala Val
            20                  25                  30

Gln Leu Glu Ile Ala Glu Thr Leu His Asn Asn Val Lys Pro Met Ser
        35                  40                  45

Leu Ser Glu Leu Ala Ser Lys Leu Pro Ala Gln Pro Val Asn Glu Asp
    50                  55                  60

Arg Leu Tyr Arg Ile Leu His Phe Leu Val His Met Lys Leu Phe Asn
65                  70                  75                  80

Lys Asp Ala Thr Thr Gln Lys Tyr Ser Leu Ala Pro Pro Ala Lys Tyr
                85                  90                  95

Leu Leu Lys Gly Trp Glu Lys Ser Met Val Pro Ser Ile Leu Ser Val
            100                 105                 110

Thr Asp Lys Asp Phe Thr Ala Pro Trp Asn His Leu Gly Asp Gly Leu
        115                 120                 125

Thr Gly Asn Cys Asn Ala Phe Glu Lys Ala Leu Gly Lys Gly Ile Arg
    130                 135                 140

Val Tyr Met Arg Glu Asn Pro Glu Lys Asp Gln Leu Phe Asn Glu Gly
145                 150                 155                 160

Met Ala Cys Asp Thr Arg Leu Phe Ala Ser Ala Leu Val Asn Glu Cys
                165                 170                 175

Lys Ser Ile Phe Ser Asp Gly Ile Asn Thr Leu Ala Gly Val Gly Arg
            180                 185                 190

Gly Thr Gly Thr Ala Val Lys Ala Ile Ser Lys Ala Phe Pro Asp Ile
        195                 200                 205

Lys Cys Thr Ile His Asp Leu Pro Glu Val Thr Ser Lys Asn Ser Lys
    210                 215                 220

Ile Pro Arg Asp Val Phe Lys Ser Val Pro Ser Ala Asp Ala Ile Phe
225                 230                 235                 240

Met Lys Ser Ile Leu His Glu Trp Asn Asp Glu Glu Cys Ile Gln Ile
                245                 250                 255

Leu Lys Arg Cys Lys Glu Ala Ile Pro Lys Gly Gly Lys Val Ile Ile
            260                 265                 270
```

-continued

```
Ala Asp Val Val Ile Asp Met Asp Ser Thr His Pro Tyr Ser Lys Ser
        275                 280                 285

Arg Leu Ala Met Asp Leu Ala Met Met Leu His Thr Gly Gly Lys Glu
    290                 295                 300

Arg Thr Glu Glu Asp Trp Lys Lys Leu Ile Asp Ala Ala Gly Phe Ala
305                 310                 315                 320

Ser Cys Lys Ile Thr Lys Leu Ser Ala Leu Gln Ser Val Ile Glu Ala
                325                 330                 335

Tyr Pro His


<210> SEQ ID NO 10
<211> LENGTH: 622
<212> TYPE: DNA
<213> ORGANISM: Papaver somniferum

<400> SEQUENCE: 10

gaggtgttca ttgccatgtc aaaggcatta aacttcataa acccagatga gctttcgatg      60

cagtgcattt tgatagcttt gaaccgtttc cttcaggaaa agcatggttc caagatggcc     120

tttttagatg gtaatcctcc cgagagactt tgcaagccgg tcgtggatca tatagagtca     180

cttggcggtg aagtccgtct caattccagg attaaaaaga ttgagcttaa aaaagatggt     240

actgtgaaac gtctaatgct caccaacggt gatgcaatag aaggagatgc ttatgtcatt     300

gcaaccccag tggacatcct aaagctgctt atacccgagg agtggaaaga agttgggtac     360

tttaaaagat tggataaatt agttggagtt cctgtgatta acgtccatat atggtttgac     420

aggaaattga aaaatacata tgatcatctt ctcttcagca gaagtcccct cttaagcgta     480

tacgctgaca tgtcagtgac atgcaaggaa tattatgacc caaacaaatc catgcttgag     540

ttggtatttg cacccgctga ggaatggatc tcgcgcagtg actctgaaat tattgaagct     600

actatgcagg agcttgcgaa ac                                              622


<210> SEQ ID NO 11
<211> LENGTH: 350
<212> TYPE: DNA
<213> ORGANISM: Papaver somniferum

<400> SEQUENCE: 11

tggtcataat catcaatcag ccacagtcac taaaatcact gcttctaatg aaagcagcaa      60

tggtgtctgt tatctttcag aaacggctaa cttggggaag ttaatatgca ttccaatggc     120

actaagagct gcgatggagc taaatgtgtt ccaacttatc tcaaagttcg gaactgacgc     180

aaaagtttcg gcttctgaaa ttgcctctaa aatgccaaac gcgaagaata atcctgaagc     240

agctatgtat ttggatagaa ttcttcgact gctcggggca agttctattc tttctgtttc     300

tactacaaaa aaatcaatca acagaggagg agatgatgta gtagtacatg                350


<210> SEQ ID NO 12
<211> LENGTH: 213
<212> TYPE: DNA
<213> ORGANISM: Papaver somniferum

<400> SEQUENCE: 12

gtgtaactaa gccagcgcta atacaaggat gtggcaaaat cctgaacgga gttacatcgt      60

taattgatgt cggtggtggt cacggtgcca ctatggccta catagttgaa gcttttcctc     120

acataaaagg tgcggtaatc gatttaccac atgttgttga agccgctccg gagcgtccag     180

gtgttgagtt catcagcggt gatatattca agt                                  213
```

<210> SEQ ID NO 13
<211> LENGTH: 19
<212> TYPE: DNA
<213> ORGANISM: Papaver somniferum

<400> SEQUENCE: 13
ctctaaaatg ccaaacgcg 19

<210> SEQ ID NO 14
<211> LENGTH: 20
<212> TYPE: DNA
<213> ORGANISM: Papaver somniferum

<400> SEQUENCE: 14
gaccctttgg gacttcctcg 20

<210> SEQ ID NO 15
<211> LENGTH: 19
<212> TYPE: DNA
<213> ORGANISM: Papaver somniferum

<400> SEQUENCE: 15
cgtgttgttt ggtccctcg 19

<210> SEQ ID NO 16
<211> LENGTH: 21
<212> TYPE: DNA
<213> ORGANISM: Papaver somniferum

<400> SEQUENCE: 16
aaatcgttcg ctctttaccg c 21

<210> SEQ ID NO 17
<211> LENGTH: 23
<212> TYPE: DNA
<213> ORGANISM: Papaver somniferum

<400> SEQUENCE: 17
gattcccgat ttactcctga tgg 23

<210> SEQ ID NO 18
<211> LENGTH: 30
<212> TYPE: DNA
<213> ORGANISM: Papaver somniferum

<400> SEQUENCE: 18
aacacaaaat acgattactt acttttgtcc 30

<210> SEQ ID NO 19
<211> LENGTH: 23
<212> TYPE: DNA
<213> ORGANISM: Papaver somniferum

<400> SEQUENCE: 19
tgcctcatgt tatttctgtt gcc 23

<210> SEQ ID NO 20
<211> LENGTH: 26
<212> TYPE: DNA
<213> ORGANISM: Papaver somniferum

<400> SEQUENCE: 20

```
gcatgaaatg gatgtagtta tcttgg                                    26


<210> SEQ ID NO 21
<211> LENGTH: 22
<212> TYPE: DNA
<213> ORGANISM: Papaver somniferum

<400> SEQUENCE: 21

cacaccaaac ttgatcattg tc                                        22


<210> SEQ ID NO 22
<211> LENGTH: 23
<212> TYPE: DNA
<213> ORGANISM: Papaver somniferum

<400> SEQUENCE: 22

gcacactgtc tttttcttcc acc                                       23


<210> SEQ ID NO 23
<211> LENGTH: 19
<212> TYPE: DNA
<213> ORGANISM: Papaver somniferum

<400> SEQUENCE: 23

ctctaaaatg ccaaacgcg                                            19


<210> SEQ ID NO 24
<211> LENGTH: 19
<212> TYPE: DNA
<213> ORGANISM: Papaver somniferum

<400> SEQUENCE: 24

cgtgttgttt ggtccctcg                                            19


<210> SEQ ID NO 25
<211> LENGTH: 23
<212> TYPE: DNA
<213> ORGANISM: Papaver somniferum

<400> SEQUENCE: 25

gattcccgat ttactcctga tgg                                       23


<210> SEQ ID NO 26
<211> LENGTH: 23
<212> TYPE: DNA
<213> ORGANISM: Papaver somniferum

<400> SEQUENCE: 26

tgcctcatgt tatttctgtt gcc                                       23


<210> SEQ ID NO 27
<211> LENGTH: 22
<212> TYPE: DNA
<213> ORGANISM: Papaver somniferum

<400> SEQUENCE: 27

cacaccaaac ttgatcattg tc                                        22


<210> SEQ ID NO 28
<211> LENGTH: 23
<212> TYPE: DNA
<213> ORGANISM: Papaver somniferum

<400> SEQUENCE: 28
```

```
gcacactgtc tttttcttcc acc                                          23


<210> SEQ ID NO 29
<211> LENGTH: 20
<212> TYPE: DNA
<213> ORGANISM: Papaver somniferum

<400> SEQUENCE: 29

gaccctttgg gacttcctcg                                              20


<210> SEQ ID NO 30
<211> LENGTH: 21
<212> TYPE: DNA
<213> ORGANISM: Papaver somniferum

<400> SEQUENCE: 30

aaatcgttcg ctctttaccg c                                            21


<210> SEQ ID NO 31
<211> LENGTH: 30
<212> TYPE: DNA
<213> ORGANISM: Papaver somniferum

<400> SEQUENCE: 31

aacacaaaat acgattactt acttttgtcc                                   30


<210> SEQ ID NO 32
<211> LENGTH: 26
<212> TYPE: DNA
<213> ORGANISM: Papaver somniferum

<400> SEQUENCE: 32

gcatgaaatg gatgtagtta tcttgg                                       26


<210> SEQ ID NO 33
<211> LENGTH: 27
<212> TYPE: DNA
<213> ORGANISM: Papaver somniferum

<400> SEQUENCE: 33

attgttgata ttgaatcaga aactttc                                      27


<210> SEQ ID NO 34
<211> LENGTH: 25
<212> TYPE: DNA
<213> ORGANISM: Papaver somniferum

<400> SEQUENCE: 34

tcaataccag tactgttagt ttccg                                        25


<210> SEQ ID NO 35
<211> LENGTH: 27
<212> TYPE: DNA
<213> ORGANISM: Papaver somniferum

<400> SEQUENCE: 35

gcaactgttt cattaacagg cacatcc                                      27


<210> SEQ ID NO 36
<211> LENGTH: 22
<212> TYPE: DNA
<213> ORGANISM: Papaver somniferum
```

<400> SEQUENCE: 36
attgatgtcg gtggtggtca cg 22

<210> SEQ ID NO 37
<211> LENGTH: 24
<212> TYPE: DNA
<213> ORGANISM: Papaver somniferum

<400> SEQUENCE: 37
ccacatcctt gtattagcgc tggc 24

<210> SEQ ID NO 38
<211> LENGTH: 29
<212> TYPE: DNA
<213> ORGANISM: Papaver somniferum

<400> SEQUENCE: 38
cagtaaattc acacattccg tatcttccc 29

<210> SEQ ID NO 39
<211> LENGTH: 24
<212> TYPE: DNA
<213> ORGANISM: Papaver somniferum

<400> SEQUENCE: 39
attcccgttc aagtaaacat gcgg 24

<210> SEQ ID NO 40
<211> LENGTH: 28
<212> TYPE: DNA
<213> ORGANISM: Papaver somniferum

<400> SEQUENCE: 40
accggaatga gaatgcataa agtaaagg 28

<210> SEQ ID NO 41
<211> LENGTH: 27
<212> TYPE: DNA
<213> ORGANISM: Papaver somniferum

<400> SEQUENCE: 41
attgtatagc caaagttgca ggtaggg 27

<210> SEQ ID NO 42
<211> LENGTH: 23
<212> TYPE: DNA
<213> ORGANISM: Papaver somniferum

<400> SEQUENCE: 42
agaccgtttg taccgaattc tgc 23

<210> SEQ ID NO 43
<211> LENGTH: 24
<212> TYPE: DNA
<213> ORGANISM: Papaver somniferum

<400> SEQUENCE: 43
gcttcagcat tggttaacga gtgc 24

<210> SEQ ID NO 44
<211> LENGTH: 23
<212> TYPE: DNA
<213> ORGANISM: Papaver somniferum

<400> SEQUENCE: 44
gcagtgaaag ccatatccaa agc 23

<210> SEQ ID NO 45
<211> LENGTH: 21
<212> TYPE: DNA
<213> ORGANISM: Papaver somniferum

<400> SEQUENCE: 45
aaccgtcccc aagatgattc c 21

<210> SEQ ID NO 46
<211> LENGTH: 22
<212> TYPE: DNA
<213> ORGANISM: Papaver somniferum

<400> SEQUENCE: 46
tcgttccatt cgtgaagaat gc 22

<210> SEQ ID NO 47
<211> LENGTH: 26
<212> TYPE: DNA
<213> ORGANISM: Papaver somniferum

<400> SEQUENCE: 47
gagggtaagc ctcaataaca gactgg 26

<210> SEQ ID NO 48
<211> LENGTH: 25
<212> TYPE: DNA
<213> ORGANISM: Papaver somniferum

<400> SEQUENCE: 48
ttaagatcac caggcatact caagg 25

<210> SEQ ID NO 49
<211> LENGTH: 22
<212> TYPE: DNA
<213> ORGANISM: Papaver somniferum

<400> SEQUENCE: 49
gaggtgttca ttgccatgtc aa 22

<210> SEQ ID NO 50
<211> LENGTH: 22
<212> TYPE: DNA
<213> ORGANISM: Papaver somniferum

<400> SEQUENCE: 50
gtttcgcaag ctcctgcata gt 22

<210> SEQ ID NO 51
<211> LENGTH: 34
<212> TYPE: DNA
<213> ORGANISM: Papaver somniferum

<400> SEQUENCE: 51
aaactcgaga agcttggtca taatcatcaa tcag 34

<210> SEQ ID NO 52
<211> LENGTH: 31
<212> TYPE: DNA

-continued

```
<213> ORGANISM: Papaver somniferum

<400> SEQUENCE: 52

aaaggtaccc atgtactact acatcatctc c                                  31


<210> SEQ ID NO 53
<211> LENGTH: 33
<212> TYPE: DNA
<213> ORGANISM: Papaver somniferum

<400> SEQUENCE: 53

aaactcgaga agcttgtgta actaagccag cgc                                33


<210> SEQ ID NO 54
<211> LENGTH: 27
<212> TYPE: DNA
<213> ORGANISM: Papaver somniferum

<400> SEQUENCE: 54

aaaggtacca cttgaatata tcaccgc                                       27


<210> SEQ ID NO 55
<211> LENGTH: 33
<212> TYPE: DNA
<213> ORGANISM: ARTIFICIAL
<220> FEATURE:
<223> OTHER INFORMATION: oligo T primer used for synthesis of cDNA

<400> SEQUENCE: 55

attctagatc cracatgttt ttttttttt ttt                                 33


<210> SEQ ID NO 56
<211> LENGTH: 28
<212> TYPE: DNA
<213> ORGANISM: Papaver somniferum

<400> SEQUENCE: 56

ataggatcca acatggctac caatggcg                                      28


<210> SEQ ID NO 57
<211> LENGTH: 22
<212> TYPE: DNA
<213> ORGANISM: Papaver somniferum

<400> SEQUENCE: 57

gcgctcgagc attcatttgt ga                                            22
```

METHYLTRANSFERASE NUCLEIC ACIDS AND POLYPEPTIDES

CROSS REFERENCE TO RELATED APPLICATIONS

This is the U.S. National Stage of International Application No. PCT/GB2011/051121, filed Jun. 16, 2011, which was published in English under PCT Article 21(2), which in turn claims the benefit of Great Britain Application No. 1010471.9, filed Jun. 22, 2010 and Great Britain Application No. 1021720.6, filed Dec. 22, 2010.

INTRODUCTION

This disclosure relates to the isolation and sequencing of nucleic acid molecules that encode methyltransferase polypeptides from a *Papaver somniferum* cultivar, [poppy plant]; transgenic cells transformed with said nucleic acid molecules, sequence variants of the genes; the use of said genes/proteins in the production of noscapine and the use of the genes as markers of poppy plants that synthesize noscapine.

BACKGROUND

The opium poppy *P. somniferum* is the plant from which opium is extracted. The opium poppy is the only commercially exploited poppy of the family Papaveraceae and is the principal source of natural opiates. The opium is extracted from latex harvested from the green seed pods. A further source of opiate alkaloids is the poppy straw which is the dried mature plant. *P. somniferum* is a source of clinically useful opiate alkaloids such as morphine, codeine, thebaine, noscapine [also known as narcotine] and papaverine. The clinical application of these opiate alkaloids and their derivates is broad having use as analgesics, cough suppressants and anti-spasmodics. Although not used as a pharmacological agent in its own right, thebaine is a particularly useful opiate which can be converted into a range of compounds such as hydrocodone, oxycodone, oxymorphone, nalbuphine naltrexone, buprenorphine and etorphine. These intermediates also have broad pharmaceutical applications. For example, oxycodone, oxymorphone and etorphine are widely used as an analgesic for moderate to severe pain and are often combined with other analgesics such as ibuprofen. Buprenorphine is used in the treatment of heroin addiction and chronic pain. Naltrexone is used in the treatment of alcohol and opiate addiction.

The use of thebaine in the production of these compounds is limited since thebaine is a minor component of the opiates extracted from poppy straw only accounting for approximately 0.5-2% of the opium extracted from dry straw. Mutant varieties of *P. somniferum* have been developed that can obtain thebaine and oripavine content of at least 50% by weight of the alkaloid combination of morphine, codeine, thebaine and oripavine; see WO98/02033. Alternative means to enhance the production of thebaine include the spraying of poppy plants with growth regulatory chemicals which inhibit alkaloid biosynthetic pathways to enhance the production of thebaine and other opiate alkaloids.

This disclosure relates to molecular analyses of gene expression in poppy cultivars that produce noscapine. Noscapine does not have significant analgesic properties but is used as a cough suppressant and is being investigated as an anti-cancer agent and in the treatment of stroke patients.

We have surprisingly found that certain varieties of poppy cultivars have genes that are unique to those cultivars that produce noscapine. We have cloned three genes that have homology to methyltransferases.

The first methyltransferase, PSMT1, exhibits sequence similarity to S-Adenosyl-L-Methionine:Scoulerine-9-O-Methyltransferase from *Coptis japonica* (Accession: Q39522.1, 61% identical) and from *Thalictrum flavum* (Accession: AAU20770.1, 59% identical). The protein from *Coptis japonica* has been characterised and shown to catalyse the transfer of the S-methyl group of S-adenosyl-L-methionine to the 9-hydroxyl group of scoulerine to form tetrahydrocolumbamine (Sato et al. (1993) Phytochem. 32:659-664) which, in turn, serves as the precursor for the synthesis of most protoberberine alkaloids.

The second methyltransferase, PSMT2, exhibits sequence similarity to S-Adenosyl-L-Methionine:Norcoclaurine-6-O-Methyltransferase from *Coptis japonica* (Accession: Q9LEL6, 42% identical) which has been shown to catalyse the transfer of the S-methyl group of S-adenosyl-L-methionine to the 6-hydroxyl group of (S)-Norcoclaurine to form (S)-Coclaurine (Morishige et al. (2000) J. Biol. Chem. 275(30): 23398-23405).

The third methyltransferase, PSMT3, exhibits sequence similarity to S-Adenosyl-L-Methionine:Norcoclaurine-6-O-Methyltransferase from *Papaver somniferum* (Accession: AAQ01669, 80% identical) and *Papaver bracteatum* (Accession: ACO90232, 80% identical). The protein from *Papaver somniferum* has been characterised and shown to catalyse the transfer of the S-methyl group of S-adenosyl-L-methionine to to catalyse the transfer of the S-methyl group of S-adenosyl-L-methionine to the 6-hydroxyl group of (S)-Norcoclaurine to form (S)-Coclaurine (Ounaroon et al. (2003) 36:808-819).

STATEMENTS OF INVENTION

According to an aspect of the invention there is provided an isolated nucleic acid molecule that encodes a methyltransferase polypeptide wherein said nucleic acid molecule comprises or consists of a nucleotide sequence selected from the group consisting of:

i) a nucleotide sequence as represented by the sequence in FIG. 1*a*, 1*b* 1*c*, 3*a*, 3*b* or 3*c;* ii) a nucleotide sequence wherein said sequence is degenerate as a result of the genetic code to the nucleotide sequence defined in (i);

iii) a nucleic acid molecule the complementary strand of which hybridizes under stringent hybridization conditions to the sequence in FIG. 1*a*, 1*b*, 1*c*, 3*a*, 3*b* or 3*c* wherein said nucleic acid molecule encodes a methyltransferase polypeptide;

iv) a nucleotide sequence that encodes a polypeptide comprising an amino acid sequence as represented in FIG. 4*a*, 4*b* or 4*c;* v) a nucleotide sequence that encodes a polypeptide comprising an amino acid sequence wherein said amino acid sequence is modified by addition deletion or substitution of at least one amino acid residue as represented in iv) above and which has retained or enhanced methy transferase activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, N.Y., 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Allows Sequences that Share at Least 80% Identity to Hybridize)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Allows Sequences that Share at Least 50% Identity to Hybridize)

Hybridization: 6×SSC at RT to 55° C. for 16-20 hours

Wash at least twice: 2×-3×SSC at RT to 55° C. for 20-30 minutes each.

In a preferred embodiment of the invention said nucleic acid molecule comprises or consists of a nucleotide sequence as represented in FIG. 1*a*, 1*b*, 1*c*, 3*a*, 3*b* or 3*c*.

According to a further aspect of the invention there is provided an isolated polypeptide selected from the group consisting of:

i) a polypeptide comprising or consisting of an amino acid sequence as represented in FIG. 4*a*, 4*b* or 4*c*; or ii) a modified polypeptide comprising or consisting of a modified amino acid sequence wherein said polypeptide is modified by addition deletion or substitution of at least one amino acid residue of the sequence presented in FIG. 4*a*, 4*b* or 4*c* and which has retained or enhanced methyltransferase activity.

A modified polypeptide as herein disclosed may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 43% identity, more preferably at least 62% identity, even more preferably at least 70% identity, still more preferably at least 75%, 80%, 85%, 90%, 95% identity, and most preferably at least 99% identity with the full length amino acid sequence illustrated herein.

According to a further aspect of the invention there is provided a vector comprising a nucleic acid molecule encoding a methyltransferase according to the invention wherein said nucleic acid molecule is operably linked with a nucleic acid sequence comprising a promoter sequence.

In a preferred embodiment of the invention said nucleic acid sequence comprising a promoter confers constitutive expression on said methyltransferase.

In an alternative preferred embodiment of the invention said nucleic acid sequence comprising a promoter confers regulated expression on said methyltransferase.

In a preferred embodiment of the invention said regulated expression is tissue or developmentally regulated expression.

In a further alternative embodiment of the invention said regulated expression is inducible expression.

In an alternative embodiment of the invention a vector including nucleic acid according to the invention need not include a promoter or other regulatory sequence, particularly if the vector is to be used to introduce the nucleic acid into cells for recombination into the gene.

Preferably the nucleic acid in the vector is under the control of, and operably linked to, an appropriate promoter or other regulatory elements for transcription in a host cell such as a microbial, (e.g. bacterial, yeast), or plant cell. The vector may be a bi-functional expression vector which functions in multiple hosts. In the case of methyltransferase genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313: 9810-812); rice actin (McElroy et al. (1990) Plant Cell 2: 163-171); ubiquitin (Christian et al. (1989) Plant Mol. Biol. 18: 675-689); pEMU (Last et al. (1991) Theor Appl. Genet. 81: 581-588); MAS (Velten et al. (1984) EMBO J. 3: 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is a tissue specific promoter, an inducible promoter or a developmentally regulated promoter.

Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809).

If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

According to a further aspect of the invention there is provided a transgenic cell transformed or transfected with a nucleic acid molecule or vector according to the invention.

In a preferred embodiment of the invention said cell is a plant cell.

In a preferred embodiment of the invention said plant cell is from the family Papaveraceae.

In a preferred embodiment of the invention said plant cell is a *Papaver somniferum* cell.

According to a further aspect of the invention there is provided a plant comprising a plant cell according to the invention.

In a preferred embodiment of the invention said plant is from the family Papaveraceae; preferably *Papaver somniferum.*

In an alternative preferred embodiment of the invention said cell is a microbial cell; preferably a bacterial or fungal cell [e.g. yeast, *Saccharomyces cerevisae].*

According to a further aspect of the invention there is provided a nucleic acid molecule comprising a transcription cassette wherein said cassette includes a nucleotide sequence designed with reference to FIG. 1*a*, 1*b*, 1*c*, 3*a*, 3*b* or 3*c* and is adapted for expression by provision of at least one promoter operably linked to said nucleotide sequence such that both sense and antisense molecules are transcribed from said cassette.

In a preferred embodiment of the invention said cassette is adapted such that both sense and antisense nucleic acid molecules are transcribed from said cassette wherein said sense and antisense nucleic acid molecules are adapted to anneal over at least part or all of their length to form a siRNA or shRNA.

In a preferred embodiment of the invention said cassette is provided with at least two promoters adapted to transcribe both sense and antisense strands of said nucleic acid molecule.

In an alternative preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an RNA molecule which forms a double stranded region by complementary base pairing of said first and second parts thereby forming an shRNA.

A technique to specifically ablate gene function is through the introduction of double stranded RNA, also referred to as small inhibitory/interfering RNA (siRNA) or short hairpin RNA [shRNA], into a cell which results in the destruction of mRNA complementary to the sequence included in the siRNA/shRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said nucleic acid molecule is part of a vector adapted for expression in a plant cell.

According to a further aspect of the invention there is provided a plant cell transfected with a nucleic acid molecule or vector according to the invention wherein said cell has reduced expression of said methyltransferase.

According to an aspect of the invention there is provided a process for the methylation of an opiate alkaloid comprising:

i) providing a transgenic plant cell according to the invention;
ii) cultivating said plant cell to produce a transgenic plant; and optionally
i) harvesting said transgenic plant, or part thereof.

In a preferred method of the invention said harvested plant material is dried straw and said opiate alkaloid is extracted.

According to an alternative aspect of the invention there is provided a process for the methylation of an opiate alkaloid comprising:

i) providing a transgenic microbial cell according to the invention that expresses a methy transferase according to the invention in culture with at least one opiate alkaloid;
ii) cultivating the microbial cell under conditions that methylate one or more opiate alkaloids; and optionally
iii) isolating said methylated alkaloid from the microbial cell or cell culture.

In a preferred method of the invention said microbial cell is a bacterial cell or fungal/yeast cell.

If microbial cells are used as organisms in the process according to the invention they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The methylated opiate alkaloids produced can be isolated from the organisms as described above by processes known to the skilled worker, for example by extraction, distillation, crystallization, if appropriate precipitation with salt, and/or chromatography. To this end, the organisms can advantageously be disrupted beforehand. In this process, the pH value is advantageously kept between pH 4 and 12, preferably between pH 6 and 9, especially preferably between pH 7 and 8.

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the opiate alkaloids present therein.

According to a further aspect of the invention there is provided the use of a gene encoded by a nucleic acid molecule as represented by the nucleic acid sequence in FIG. 3a, 3b or 3c, or a nucleic acid molecule that hybridizes under stringent hybridization conditions to the nucleotide sequence in FIG. 3a, 3b or 3c and encodes a polypeptide with methyltransferase activity as a means to identify the presence or absence of a gene that encodes said methyltransferase in a Papaveraceae plant.

According to a further aspect of the invention there is provided a method to determine the presence or absence of a gene according to the invention in a Papaveraceae variety comprising:

i) obtaining a sample from a Papaveraceae plant;
ii) extracting genomic DNA from the plant; and
iii) analyzing the genomic DNA for the presence of a gene comprising or consisting of a nucleotide sequence as represented in FIG. 3a, 3b or 3c.

Methods to analyze genomic DNA are well known in the art. For example, polymerase chain reaction methods using sequence specific oligonucleotide primers to amplify specific regions of the gene according to the invention. The extraction, isolation and restriction analysis using sequence specific restriction endonucleases followed by separation and Southern blotting to analyze genomic structure have been established for over thirty years. The analysis may be directed to intron or exon structure or upstream or downstream regions of the gene; e.g. promoter regions.

According to a further aspect of the invention there is provided the use of a gene encoded by a nucleic acid molecule as represented by the nucleic acid sequence in FIG. 3a, 3b or 3c, or a nucleic acid molecule that hybridizes under stringent hybridization conditions to the nucleotide sequence in FIG. 3a, 3b or 3c and encodes a polypeptide with methyltransferase activity as a means to identify a locus wherein said locus is associated with altered expression or activity of said methyltransferase.

Mutagenesis as a means to induce phenotypic changes in organisms is well known in the art and includes but is not limited to the use of mutagenic agents such as chemical mutagens [e.g. base analogues, deaminating agents, DNA intercalating agents, alkylating agents, transposons, bromine, sodium azide] and physical mutagens [e.g. ionizing radiation, psoralen exposure combined with UV irradiation].

According to a further aspect of the invention there is provided a method to produce a Papaveraceae plant variety that has altered expression of a methyltransferase according to the invention comprising the steps of:

i) mutagenesis of wild-type seed from a plant that does express said methyltransferase;
ii) cultivation of the seed in i) to produce first and subsequent generations of plants;
iii) obtaining seed from the first generation plant and subsequent generations of plants;
iv) determining if the seed from said first and subsequent generations of plants has altered nucleotide sequence and/or altered expression of said methyltransferase;
v) obtaining a sample and analysing the nucleic acid sequence of a nucleic acid molecule selected from the group consisting of:
   a) a nucleic acid molecule comprising a nucleotide sequence as represented in FIG. 3a, 3b or 3c;
   b) a nucleic acid molecule that hybridises to the nucleic acid molecule in a) under stringent hybridisation conditions and that encodes a polypeptide with methyltransferase activity; and optionally
vi) comparing the nucleotide sequence of the nucleic acid molecule in said sample to a nucleotide sequence of a nucleic acid molecule of the original wild-type plant.

In a preferred method of the invention said nucleic acid molecule is analysed by a method comprising the steps of:

i) extracting nucleic acid from said mutated plants;
ii) amplification of a part of said nucleic acid molecule by a polymerase chain reaction;
iii) forming a preparation comprising the amplified nucleic acid and nucleic acid extracted from wild-type seed to form heteroduplex nucleic acid;
iv) incubating said preparation with a single stranded nuclease that cuts at a region of heteroduplex nucleic acid to identify the mismatch in said heteroduplex; and
v) determining the site of the mismatch in said nucleic acid heteroduplex.

In a preferred method of the invention said Papaveraceae plant variety has enhanced methyltransferase expression and/or activity.

According to a further aspect of the invention there is provided a plant obtained by the method according to the invention.

According to an aspect of the invention there is provided a plant wherein said plant comprises a viral vector that includes all or part of a gene comprising a nucleic acid molecule according to the invention.

In a preferred embodiment of the invention said gene is encoded by a nucleic acid molecule comprising a nucleic acid sequence selected from the group consisting of:

i) a nucleic acid molecule comprising a nucleotide sequence as represented in FIG. 1a, 1b or 1c;
ii) a nucleic acid molecule comprising a nucleotide sequence that hybridises under stringent hybridisation conditions to a nucleic acid molecule in (i) and which encodes a methytransferase polypeptide;
iii) a nucleic acid molecule that encodes a variant polypeptide that varies from a polypeptide comprising the amino acid sequence as represented in FIG. 4a, 4b or 4c.

In a preferred embodiment of the invention said nucleic acid molecule comprises or consists of a nucleotide sequence as represented in FIG. 1a.

In a preferred embodiment of the invention said nucleic acid molecule comprises or consists of a nucleotide sequence as represented in FIG. 1b.

In a preferred embodiment of the invention said nucleic acid molecule comprises or consists of a nucleotide sequence as represented in FIG. 1c In a preferred embodiment of the invention said nucleic acid molecule consists of a nucleotide sequence as represented in FIG. 14.

In an alternative preferred embodiment of the invention said nucleic acid molecule consists of a nucleotide sequence as represented in FIG. 15.

According to a further aspect of the invention there is provided a viral vector comprising all or part of a nucleic acid molecule according to the invention.

According to an aspect of the invention there is provided the use of a viral vector according to the invention in viral induced gene silencing in a plant.

In a preferred embodiment of the invention said plant is from the family Papaveraceae.

Virus induced gene silencing [VIGS] is known in the art and exploits a RNA mediated antiviral defence mechanism. Plants that are infected with an unmodified virus induces a mechanism that specifically targets the viral genome. However, viral vectors which are engineered to include nucleic acid molecules derived from host plant genes also induce specific inhibition of viral vector expression and additionally target host mRNA. This allows gene specific gene silencing without genetic modification of the plant genome and is essentially a non-transgenic modification.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1*a* (SEQ ID NO: 1) is the nucleotide sequence of a cDNA that encodes PSMT1; FIG. 1*b* (SEQ ID NO: 2) is the nucleotide sequence of a cDNA that encodes PSMT2; FIG. 1*c* (SEQ ID NO: 3) is the nucleotide sequence of a cDNA that encodes PSMT3

FIG. 2: Expression of the *P. somniferum* SAM-Scoulerine-9-O-methyltransferase gene (PSMT1). The 16 EST libraries were generated by pyrosequencing using cDNA libraries prepared from stems (S) and capsules (C) at two developmental stages 'early harvest' (EH, 1-3 days after petals had fallen off) and 'late-harvest' (LH, 4-6 days after petals had fallen off) from each of the four *P. somniferum* cultivars: GSK MORPHINE CVS1, GSK MORPHINE CVS2, GSK NOSAPINE CVS1 and GSK THEBAINE CVS1;

FIG. 3*a* (SEQ ID NO: 4) is the genomic nucleotide sequence of PSMT1; FIG. 3*b* (SEQ ID NO: 5) is the genomic nucleotide sequence of PSMT2: FIG. 3*c* (SEQ ID NO: 6) is the genomic nucleotide sequence of PSMT3;

FIG. 4*a* (SEQ ID NO: 7) is the deduced amino acid sequence of PSMT1; FIG. 4*b* (SEQ ID NO: 8) is the deduced amino acid sequence of PSMT2; FIG. 4*c* (SEQ ID NO: 9) is the deduced amino acid sequence of PSMT3;

FIG. 5: PCR-amplification of PsSOMT1 from genomic DNA of the four *Papaver somniferum* cultivars GSK MORPHINE CVS1, GSK MORPHINE CVS2, GSK NOSCAPINE CVS1, GSK THEBAINE CVS1;

FIG. 6*a* is a tabular representation of the segregation of PSMT1 gene in an F2 mapping population derived from a parental cross of cultivars GSK NOSCAPINE CVS1 and GSK THEBAINE CVS1 along with the co-segregation of the PSMT1 gene and noscapine accumulation in individual F2 plants; FIG. 6*b* is the equivalent tabular representation of the segregation of the PSMT2 gene. The PSMT2 genotyping assay failed (as indicated by the failure to amplify the internal positive control) on six DNA samples from F2 plants that were positive for PSMT1 and PSMT3 (indicated by asterisks); FIG. 6*c* is the equivalent tabular representation of the segregation of the PSMT3 gene;

Figure 9:
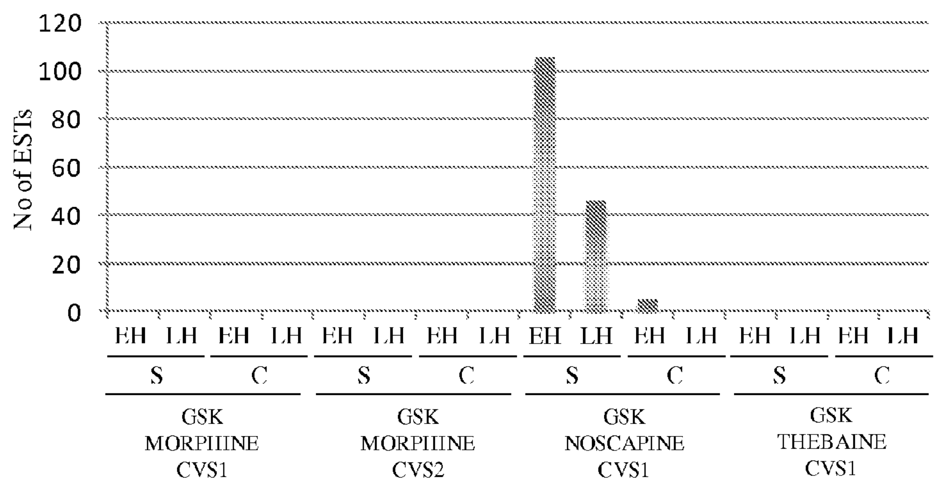
Figure 10:
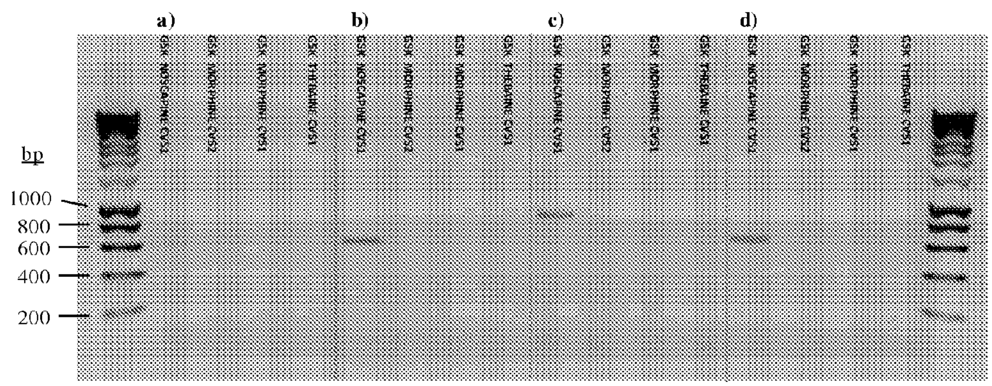
Figures 15, 16:
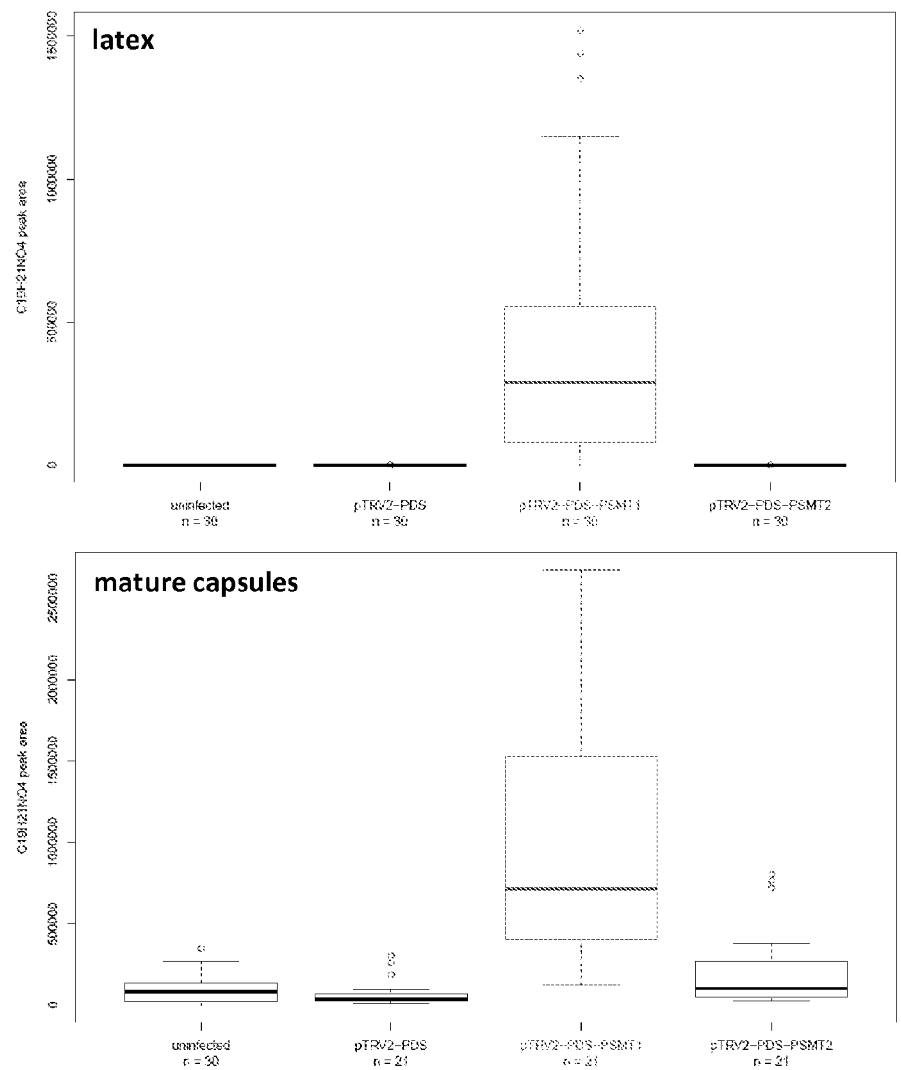
Figure 17:
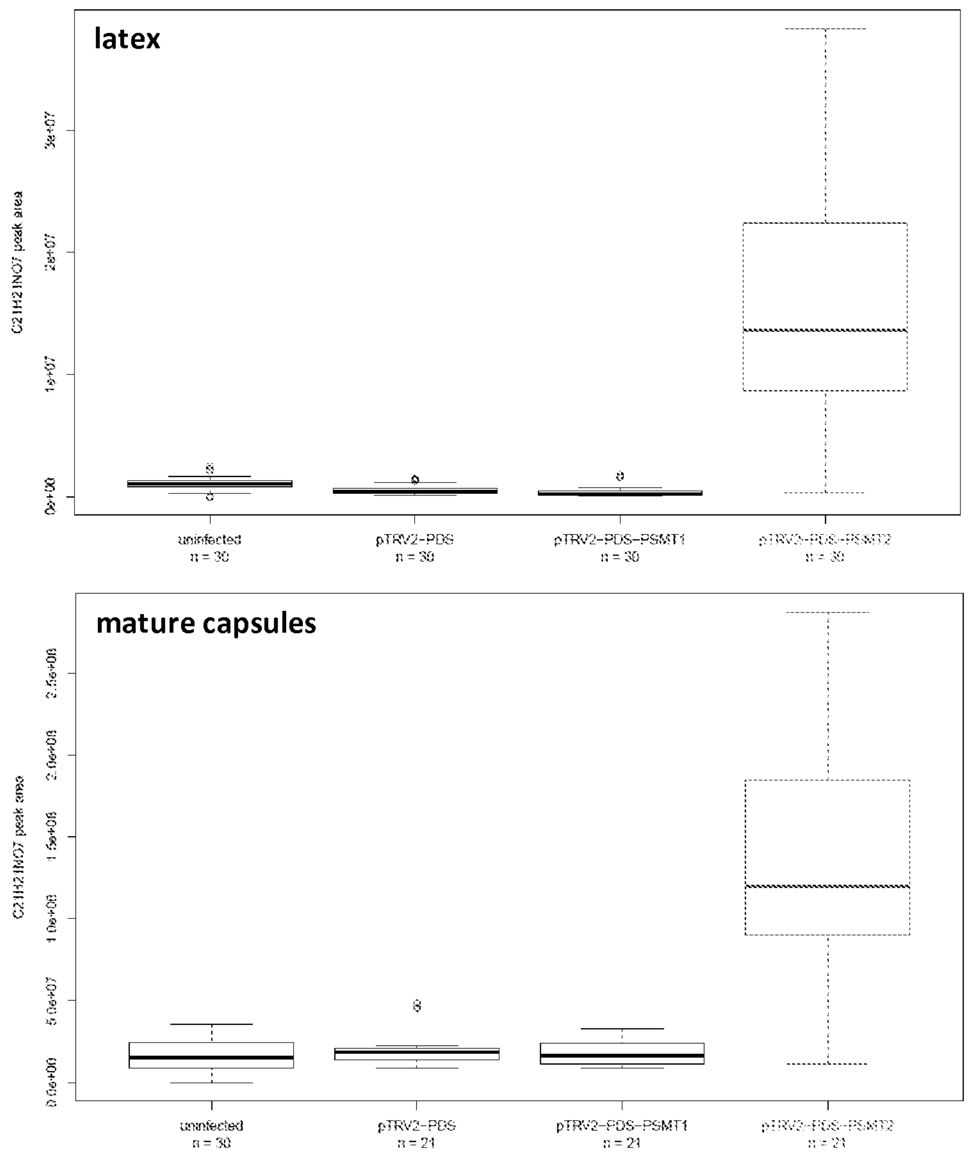

FIG. 9: Expression of the *P. somniferum* methyltransferase gene (PSMT2). The 16 EST libraries were generated by pyrosequencing using cDNA libraries prepared from stems (S) and capsules (C) at two developmental stages 'early harvest' (EH, 1-3 days after petals had fallen off) and 'late-harvest' (LH, 4-6 days after petals had fallen off) from each of the four *P. somniferum* cultivars: GSK MORPHINE CVS1, GSK MORPHINE CVS2, GSK NOSCAPINE CVS1, GSK THEBAINE CVS1;

FIG. 10 shows the results of a PCR-amplification of PSMT2 from genomic DNA of the four *Papaver somniferum* cultivars GSK MORPHINE CVS1, GSK MORPHINE CVS2, GSK NOSCAPINE CVS1, GSK THEBAINE CVS1;

FIG. 11 Expression of the *P. somniferum* methyltransferase gene (PSMT3). The 16 EST libraries were generated by pyrosequencing using cDNA libraries prepared from stems (S) and capsules (C) at two developmental stages 'early harvest' (EH, 1-3 days after petals had fallen off) and 'late-harvest' (LH, 4-6 days after petals had fallen off) from each of the four *P. somniferum* cultivars: GSK MORPHINE CVS1, GSK MORPHINE CVS2, GSK NOSCAPINE CVS1, GSK THEBAINE CVS1;

FIG. 12 shows the results of a PCR-amplification of PSMT3 from genomic DNA of the four *Papaver somniferum* cultivars GSK MORPHINE CVS1, GSK MORPHINE CVS2, GSK NOSCAPINE CVS1, GSK THEBAINE CVS1;

FIG. 13 (SEQ ID NO: 10) is the 622 bases long part of the PHYTOENE DESATURASE gene sequence amplified from cDNA of GSK NOSCAPINE CVS1. The 129-bases long sequence stretch used to silence the PHYTOENE DESATURASE gene is underlined;

FIG. 14 (SEQ ID NO: 11) is the part of the cDNA sequence used to silence PSMT1;

FIG. 15 (SEQ ID NO: 12) is the part of the cDNA sequence used to silence PSMT2;

FIG. 16 shows the normalised peak area of scoulerine in the UPLC chromatograms obtained from latex and mature capsules of plants that displayed the photo-bleaching phenotype after infection with the silencing constructs pTRV2-PDS-PSMT1, pTRV2-PDS-PSMT2 or pTRV2-PDS, respectively. The scoulerine peak area obtained from uninfected plants is shown as well. 21-30 plants were analysed per construct; and FIG. 17 shows the normalised peak area of putative narcotoline in the UPLC chromatograms obtained from latex and mature capsules of plants that displayed the photo-bleaching phenotype after infection with the silencing constructs pTRV2-PDS-PSMT1, pTRV2-PDS-PSMT2 or pTRV2-PDS, respectively. The putative narcotoline peak area obtained from uninfected plants is shown as well. 21-30 plants were analysed per construct.

MATERIALS AND METHODS

Generation of EST Libraries a) RNA Isolation and cDNA Synthesis

Material was harvested from stems and capsules at two developmental stages from four poppy cultivars. RNA was prepared individually from five plants per cultivar, developmental stage and organ. The harvested material was ground in liquid nitrogen using a mortar and pestle. RNA was isolated from the ground stem or capsule preparations using a CTAB (hexadecyltrimethylammonium bromide)

based method as described in Chang et al. (1993) Plant Mol. Biol. Rep. 11: 113-116 with slight modifications (three extractions with chloroform:isoamylalcohol, RNA precipitation with Lithium chloride at −20° C. over night). RNA was quantified spectrophotometrically before pooling equal amounts of RNA from five plants per cultivar, stage and organ. The pooled samples underwent a final purification step using an RNeasy Plus MicroKit (Qiagen, Crawley, UK) to remove any remaining genomic DNA from the preparations. RNA was typically eluted in 30-100 μl water. cDNA was prepared using a SMART cDNA Library Construction Kit (Clontech, Saint-Germainen-Laye, France) according to the manufacturer's instructions but using SuperScript II Reverse Transcriptase (Invitrogen, Paisley, UK) for first strand synthesis. The CDSIII PCR primer was modified to: 5' ATT CTA GAT CCR ACA TGT TTT TTT TTT TTT TTT TTT TVN 3' (SEQ ID NO: 55) where R=A or G, V=A, C or G; N=A/T or C/G. cDNA was digested with MmeI (New England Biolabs Inc., Hitchin, UK) followed by a final purification using a QIAquick PCR Purification kit (Qiagen, Crawley, UK).

b) cDNA Pyrosequencing

The Roche 454 GS-FLX sequencing platform (Branford, Conn., USA) was used to perform pyrosequencing on cDNA samples prepared from the following materials for each of the four *P. somniferum* cultivars GSK MORPHINE CVS2, GSK MORHINE CVS1, GSK NOSAPINE CVS1 and GSK THEBAINE CVS1:

1. Stem, 1-3 days after petal fall (early harvest)
2. Stem, 4-6 days after petal fall (late harvest)
3. Capsule, 1-3 days after petal fall (early harvest)
4. Capsule, 4-6 days after petal fall (late harvest)

c) Raw Sequence Analysis, Contiguous Sequence Assembly and Annotation

The raw sequence datasets were derived from parallel tagged sequencing on the 454 sequencing platform (Meyer et al. (2008) Nature Protocols 3: 267-278). Primer and tag sequences were first removed from all individual sequence reads. Contiguous sequence assembly was only performed on sequences longer than 40 nucleotides and containing less than 3% unknown (N) residues. These high quality EST sequences were assembled into unique contiguous sequences with the CAPS Sequence Assembly Program (Huang and Madan (1999) Genome Res. 9: 868-877), and the resulting contigs were annotated locally using the BLAST2 program (Altschul et al. (1997) Nucleic Acids Res. 25: 3389-3402) against the non-redundant peptide database downloaded from the NCBI.

d) Expression Profiling of the Methyltransferase Genes

The number of ESTs associated with the respective methyltransferase consensus sequences were counted in each of the 16 EST libraries. The values obtained were normalised on the basis of total ESTs obtained per library.

RT-PCR on GSK NOSAPINE CVS1 mRNA and Direct Amplification and Sequencing of Full Length cDNA of PSMT1.

An aliquot of GSK NOSAPINE CVS1 cDNA prepared for cDNA pyrosequencing (see above) was used to amplify and sequence the full length coding sequence of PSMT1 using the following PCR conditions:

| Reaction mixture: | |
|---|---|
| 5 × HF buffer (Finnzymes) | 5 μl |
| dNTPs (20 mM each) | 0.25 μl |
| Fwd primer (10 μM) | 2.5 μl |
| Rev primer (10 μM) | 2.5 μl |
| gDNA (10 ng/μl) | 5 μl |
| Phusion Hot Start (Finnzymes) | 0.25 μl |
| $dH_2O$ | 9.5 μl |
| Reaction volume: | 25 μl |

Phusion Hot Start from Finnzymes was purchased through New England Biolabs, (Bishops Stortford, UK).

PCR Programs:

| | | | |
|---|---|---|---|
| | initial denaturation | 98° C. | 1 min |
| 30 cycles of: | denaturation | 98° C. | 30 sec |
| | annealing temperature | 61° C. | 30 sec |
| | extension | 72° C. | 40 sec |
| | final extension | 72° C. | 10 min |
| | incubation | 4° C. | storage |
| primer combination: | PSMT1_CLF: ATAGGATCCAACATGGCTACCAATGGCG (SEQ ID NO: 56)<br>PSMT1_CLR: GCGCTCGAGCATTCATTTGTGA (SEQ ID NO: 57) | | |

These primers served a dual purpose in that they were used to amplify PSMT1 cDNA for sequencing and cloning (cloning not described here). The underlined bases of the cloning primers delineate the nucleotides which are sequence-specific to the 5' and 3' end of PSMT1 cDNA, respectively. The PSMT1 specific nucleotide sequence used to design the primers were confirmed upon sequencing the PSMT1 gene from genomic DNA as described below.

PCR products were cleaned with Agencourt AMPure® PCR purification kit (Beckman Coulter, High Wycombe, UK) and sequenced by Sanger sequencing.

Amplification and Sequencing of the Methyltransferase Genes from Genomic DNA a) Genomic DNA Preparation Leaf samples (30-50 mg) for DNA extraction were harvested from plants of GSK MORHINE CVS1, GSK MORPHINE CVS2, GSK NOSAPINE CVS1 and GSK THEBAINE CVS1 grown in the glasshouse. DNA was extracted using Qiagen BioSprint 96. Extracted DNA was quantified using Hoescht 33258 and normalized to 10 ng/ul.

b) Amplification and Sequencing of the Methyltransferase Genes from Genomic DNA of GSK NOSCAPINE CVS1

Primers and primer sequences used for amplification of the respective methyltransferase genes from the extracted genomic DNA are shown in Table 1. Primers were designed based on the respective methlytransferase contigs assembled from ESTs unique to cultivar GSK NOSCAPINE CVS1. The respective contigs contained the complete open reading frame of each methyltransferase as well as 5' and 3' untranslated regions. Amplification from genomic DNA was performed using the primer combinations shown in Table 2 and the PCR conditions shown below. The PCR amplifications were performed on pools of genomic DNA comprising DNA from four individuals. 5 μl of each PCR reaction was resolved on 1.2% Agarose alongside appropriate size standards.

| Reaction mixture: | |
|---|---|
| 5 × HF buffer (Finnzymes) | 5 μl |
| dNTPs (20 mM each) | 0.25 μl |
| Forward primer (10 μM) | 2.5 μl |
| Revers primer (10 μM) | 2.5 μl |
| gDNA (10 ng/μl) | 5 μl |
| Phusion Hot Start (Finnzymes) | 0.25 μl |
| $dH_2O$ | 9.5 μl |
| Reaction volume: | 25 μl |

PCR Program:

The annealing temperature and extension time for the respective primer combinations are shown in Table 2 and 3.

| | | | |
|---|---|---|---|
| 30 cycles of: | initial denaturation | 98° C. | 1 min |
| | denaturation | 98° C. | 30 sec |
| | annealing temperature | Table 2 & 3 | 30 sec |
| | extension | 72° C. | Table 2 & 3 |
| | final extension | 72° C. | 10 min |
| | incubation | 4° C. | storage |

TABLE 1

Sequences of forward and reverse primers used to amplify PsSOMT from genomic DNA for sequencing

| Primer name | Oligonucleotide sequences (5'- to 3'-) (SEQ ID NO:) | Primer combination | Expected fragment size for primer combination |
|---|---|---|---|
| SOMT_F2 | CTCTAAAATGCCAAACGCG (13) | 1 | 739 bp |
| SOMT_R2 | GACCCTTTGGGACTTCCTCG (14) | | |
| SOMT_F3 | CGTGTTGTTTGGTCCCTCG (15) | 2 | 1568 bp |
| SOMT_R3 | AAATCGTTCGCTCTTTACCGC (16) | | |
| SOMT_F4 | GATTCCCGATTTACTCCTGATGG (17) | 3 | 318 bp |
| SOMT_R4 | AACACAAAATACGATTACTTACTTTTGTCC (18) | | |
| SOMT_F5 | TGCCTCATGTTATTTCTGTTGCC (19) | 4 | 1354 bp |
| SOMT_R5 | GCATGAAATGGATGTAGTTATCTTGG (20) | | |
| SOMT_F6 | CACACCAAACTTGATCATTGTC (21) | 5 | 604 bp |
| SOMT_R1 | GCACACTGTCTTTTTCTTCCACC (22) | | |

TABLE 2

Sequences of forward and reverse primers used to amplify PS METHYLTRANSFERASEs from genomic DNA

| Methyltransferase gene | Primer name | Oligonucleotide sequences (5'- to 3'-) (SEQ ID NO:) |
|---|---|---|
| PSMT1 | PSMT1_F2 | CTCTAAAATGCCAAACGCG (23) |
| | PSMT1_F3 | CGTGTTGTTTGGTCCCTCG (24) |
| | PSMT1_F4 | GATTCCCGATTTACTCCTGATGG (25) |
| | PSMT1_F5 | TGCCTCATGTTATTTCTGTTGCC (26) |
| | PSMT1_F6 | CACACCAAACTTGATCATTGTC (27) |
| | PSMT1_R1 | GCACACTGTCTTTTTCTTCCACC (28) |
| | PSMT1_R2 | GACCCTTTGGGACTTCCTCG (29) |
| | PSMT1_R3 | AAATCGTTCGCTCTTTACCGC (30) |
| | PSMT1_R4 | AACACAAAATACGATTACTTACTTTTGTCC (31) |
| | PSMT1_R5 | GCATGAAATGGATGTAGTTATCTTGG (32) |
| PSMT2 | PSMT2_F1 | ATTGTTGATATTGAATCAGAAACTTTC (33) |
| | PSMT2_F2 | TCAATACCAGTACTGTTAGTTTCCG (34) |
| | PSMT2_F4 | GCAACTGTTTCATTAACAGGCACATCC (35) |
| | PSMT2_F5 | ATTGATGTCGGTGGTGGTCACG (36) |
| | PSMT2_R3 | CCACATCCTTGTATTAGCGCTGGC (37) |
| | PSMT2_R4 | CAGTAAATTCACACATTCCGTATCTTCCC (38) |
| | PSMT2_R5 | ATTCCCGTTCAAGTAAACATGCGG (39) |
| | PSMT2_R6 | ACCGGAATGAGAATGCATAAAGTAAAGG (40) |

TABLE 2-continued

Sequences of forward and reverse primers used to amplify PS METHYLTRANSFERASEs from genomic DNA

| Methyltransferase gene | Primer name | Oligonucleotide sequences (5'- to 3'-) (SEQ ID NO:) |
|---|---|---|
| PSMT3 | PSMT3_F1 | ATTGTATAGCCAAAGTTGCAGGTAGGG (41) |
| | PSMT3_F2 | AGACCGTTTGTACCGAATTCTGC (42) |
| | PSMT3_F3 | GCTTCAGCATTGGTTAACGAGTGC (43) |
| | PSMT3_F4 | GCAGTGAAAGCCATATCCAAAGC (44) |
| | PSMT3_R1 | AACCGTCCCCAAGATGATTCC (45) |
| | PSMT3_R2 | TCGTTCCATTCGTGAAGAATGC (46) |
| | PSMT3_R3 | GAGGGTAAGCCTCAATAACAGACTGG (47) |
| | PSMT3_R5 | TTAAGATCACCAGGCATACTCAAGG (48) |

TABLE 3

Primer combinations used to amplify and sequence PS Methyltransferases from genomic DNA

| Methyltransferase | Primer combination | Annealing temperature [° C.] | Extension time [s] | Sequencing primers used for Sanger sequencing of purified PCR product |
|---|---|---|---|---|
| PSMT1 | PSMT1_F2/R2 | 62 | 60 | PSMT1_F2, PSMT1_R2 |
| | PSMT1_F3/R3 | 68 | 60 | PSMT1_F3, PSMT1_F5, PSMT1_R3 |
| | PSMT1_F4/R4 | 66 | 60 | PSMT1_F4, PSMT1_R4 |
| | PSMT1_F5/R5 | 63.5 | 60 | PSMT1_F5, PSMT1_R3 PSMT1_R5 |
| | PSMT1_F6/R1 | 62.8 | 60 | PSMT1_F6, PSMT1_R1 |
| PSMT2 | PSMT2_F1/R6 | 60 | 60 | PSMT2_F1, PSMT2_F2, PSMT2_F4, PSMT2_F5, PSMT2_R1, PSMT2_R4, PSMT2_R6 |
| PSMT3 | PSMT3_F1/R5 | 68.5 | 60 | PSMT3_F2, PSMT3_F4, PSMT3_F5, PSMT3_R1, PSMT3_R2, PSMT3_R3 |

The PCR products were purified using the Agencourt AMPure® purification kit (BECKMAN COULTER UK LTD, Bromley, UK). 30-50 ng of the respective purified PCR product were subjected to Sanger-sequencing using the primers indicated in Table 2 as sequencing primers.

The amino acid sequences of the respective methyltransferase, deduced from the open reading frame sequences confirmed by Sanger-sequencing, were compared to protein sequences deposited in the NCBI Non-15 redundant protein database using the Standard Protein BLAST programme (blastp).

c) Analysis of Genomic DNA from GSK NOSAPINE CVS1, GSK MORPHINE CVS2, GSK MORHINE CVS1 and GSK THEBAINE CVS1 for the Presence of the Methyltransferase Genes To check if the respective methyltransferase genes were present in all four cultivars, PCr amplifications were performed on genomic DNA from GSK NOSAPINE CVS1, GSK MORPHINE CVS2, GSK MORHINE CVS1 and GSK THEBAINE CVS1. using the primer combinations shown in Table 3. Exactly the same PCR conditions as described above to amplify the full length genomic sequences from GSK NOSAPINE CVS1 were used. The genomic DNA was derived from four individual plants per cultivar. 5 μl of each PCR reaction was resolved on 1% agarose alongside appropriate size standards.

Analysis of Genomic DNA and Alkaloid Profiling from Poppy Straw of an F2 Population a) DNA Extraction from F2 Plants 40-50 mg of leaf tissue was harvested, in duplicate, from all poppy plants within the GSK NOSCAPINE CVS1×GSK THEBAINE CVS1 F2 mapping population at the 'small rosette' growth stage (~10 leaves present on each plant).

Leaf tissue (40-50 mg wet weight) was collected into 1.2 ml sample tubes in 8×12 format (Part Number 1760-00, Scientific Specialties Inc, 130 Thurman St, Lodi, Calif. 95240 USA), closed with strip caps (Part Number 1702-00, Scientific Specialties Inc) and shipped to the AGRF (Australian Genome Research Facility) Adelaide on Techni-Ice dry Ice packs by overnight courier.

On receipt, strip caps were removed and a 3 mm tungsten carbide bead was added to each tube (Part Number 69997, Qiagen GmbH, Hilden, Germany). Samples were placed at −80° C. (Freezer model; Sanyo MDF-U73V) for a minimum of two hours prior to freeze-drying for 18 hr (Christ Model Alpha 2-4 LSC).

Following freeze drying, tubes were sealed with fresh strip caps (as above), and samples were powdered by bead-milling (Model "Tissue Lyser", Part Number 85300; Qiagen) at 3,000 RPM for 2×60 sec cycles separated by plate inversion. DNA extraction was performed using the "Nucleospin Plant II" system (Macherey-Nagel, GmbH & Co. KG Neumann-Neander-Straβe 6-8, 52355 Düren, Germany).

Cell lysis was performed using the supplied Buffer Set PL2/3. The manufacturer's protocol for centrifugal extraction was followed (Centrifuge model 4-K 15; Sigma Laborzentrifugen GmbH, 37520 Osterode am Harz, Germany).

The recovered DNA (12/96 samples, one sample per plate column) was checked for quality and quantity by ultra violet spectroscopy (Model Nanodrop-8000; NanoDrop products, 3411 Silverside Rd, Bancroft Building; Wilmington, Del. 19810, USA) at 230, 260 and 280 nM.

b) Genotyping of F2 DNA Samples for Presence or Absence of the Methyltransferases DNA samples from a total of 276 F2 plants were genotyped for the presence or absence of PSMT1, PSMT2 and PSMT3, respectively, by amplifying a short fragment of each of the genes. 5'-VIC-labeled forward primers were used for the amplification of each of the methyltransferase fragments, enabling the separation and analysis of the resulting fluorescently labeled PCR fragments on the 96-capillary electrophresis 3730xl DNA Analyzer system (Applied Biosystems) according to the manufacturer's instructions. In addition to the respective methyltransferase fragments, an internal positive control was amplified in each PCR assay in order to distinguish lack of amplification due to absence of the respective methyltransferase genes in a DNA sample from lack of amplification due to PCR assay failure.

The following primers were used (primer sequences are shown in Table 1):

PSMT1: PSMT1_F3/PSMT1_R1; amplified fragment size: 129 bp

PSMT2: PSMT2_F4/PSMT2_R3; amplified fragment size: 284 bp

PSMT3: PSMT3_F4/PSMT3_R2; amplified fragment size: 309 bp

The PSMT1- and PSMT3-fragments were amplified with the following PCR conditions:

| Reaction mixture: | |
|---|---|
| 5× GoTaq Buffer (Promega) | 2 µl |
| dNTPs (2.5 mM mix) | 0.5 µl |
| $MgCl_2$ (25 mM) | 0.6 µl |
| Forward primer (10 µM) | 0.5 µl |
| Revers primer (10 µM) | 0.5 µl |
| gDNA (5 ng/µl) | 2 µl |
| GoTaq (Promega) | 0.2 µl |
| $dH_2O$ | 3.7 µl |
| Reaction volume: | 10 µl |

PCR Program:

| | | | |
|---|---|---|---|
| 30 cycles of: | initial denaturation | 94° C. | 1 min |
| | denaturation | 94° C. | 30 sec |
| | annealing temperature | 62° C. | 30 sec |
| | extension | 72° C. | 20-30 sec |
| | final extension | 72° C. | 5 min |
| | incubation | 4° C. | storage |

The PSMT2-fragment was amplified with the following PCR conditions:

| Reaction mixture: | |
|---|---|
| 5× Type-it multiplex PCR mix (Qiagen) | 5 µl |
| Forward primer (10 µM) | 0.5 µl |
| Revers primer (10 µM) | 0.5 µl |
| gDNA (5 ng/µl) | 2 µl |
| $dH_2O$ | 2 µl |
| Reaction volume: | 10 µl |

PCR Program:

| | | | |
|---|---|---|---|
| 30 cycles of: | initial denaturation | 95° C. | 15 min |
| | denaturation | 95° C. | 15 sec |
| | annealing temperature | 60° C. | 30 sec |
| | extension | 72° C. | 30 sec |
| | final extension | 72° C. | 5 min |
| | incubation | 4° C. | storage |

c) Poppy Straw Analysis from F2 Plants

Poppy capsules were harvested by hand from the mapping population once capsules had dried to approximately 10% moisture on the plant. The seed was manually separated from the capsule, and capsule straw material (Poppy Straw) was then shipped to the GSK extraction facility in Port Fairy, Australia.

The poppy straw samples were then ground in a Retsch Model MM04 ball mill into a fine powder. Two gram samples of ground poppy straw were then weighed accurately (2±0.003 g) and extracted in 50 mL of a 10% acetic acid solution. The extraction suspension was shaken on an orbital shaker at 200 rpm for a minimum of 10 minutes then filtered to provide a clear filtrate. The final filtrate was passed through a 0.22 µm filter prior to analysis.

The solutions were analysed using a Waters Acquity UPLC system fitted with a Waters Acquity BEH C18 column, 2.1 mm×100 mm with 1.7 micron packing. The mobile phase used a gradient profile with eluent A consisting of 0.1% Tetrafluoroacetic acid in deionised water and eluent B consisting of 100% Acetonitrile. The mobile phase gradient conditions used are as listed in Table 2, the gradient curve number as determined using a Waters Empower chromatography software package. The flow rate was 0.6 mL per minute and the column maintained at 45 C. The injection volume was 1 µL injection volume and the alkaloids were detected using a UV detector at 285 nm.

The loss on drying (LOD) of the straw was determined by drying in an oven at 105 degrees centrigrade for 3 hours.

Gradient Flow Program:

| TIME (minutes) | % Eluent A | % Eluent B | Flow (mL/min) | Curve No |
|---|---|---|---|---|
| 0.00 | 95.0 | 5.0 | 0.60 | INITIAL |
| 0.80 | 90.0 | 10.0 | 0.60 | 6 |
| 3.40 | 75.0 | 25.0 | 0.60 | 3 |
| 3.60 | 95.0 | 5.0 | 0.60 | 6 |
| 4.00 | 95.0 | 5.0 | 0.60 | 11 |

Alkaloid concentrations for morphine, codeine, thebaine, oripavine and noscapine were determined by comparison with standard solutions and the results calculated on a dry weight basis.

Typical retention times are as follows:

| Compound | Retention Time (minutes) |
|---|---|
| Morphine | 1.14 |
| Pseudo morphine | 1.26 |
| Codeine | 1.69 |
| Oripavine | 1.80 |
| 10-Hydroxythebaine | 2.32 |
| Thebaine | 2.53 |
| Noscapine | 3.16 |

Virus Induced Gene Silencing (VIGS) of PSMT1 and PSMT2 a) Generation of Silencing Constructs

A *tobacco rattle virus* (TRV) based virus induced gene silencing system developed and described by Liu et al. (2002) Plant J. 30(4): 415-429 was used to investigate the gene function of PSMT1 and PSMT2. DNA fragments selected for silencing of PSMT1 and PSMT2, respectively, were amplified by PCR and cloned into the silencing vector pTRV2 (GenBank accession no. AF406991; Liu et al. (2002) Plant J. 30(4): 415-429). They were linked to a 129 bp-long fragment of the *P. somniferum* Phytoene desaturase gene (PsPDS) in order to silence the respective methylatransferases and PsPDS simultaneously. Plants displaying the photo-bleaching phenotype that resulted from silencing of PsPDS (Hileman et al. (2005) Plant J. 44(2): 334-341) were identified as plants successfully infected with the respective silencing constructs and selected for analysis.

Generation of the pTRV2-PDS construct: A 622 bp fragment (FIG. 13) of PsPDS was amplified from cDNA prepared from GSK NOSCAPINE CVS1 as described above using primers ps_pds_F and ps_pds_R4 (Table 4). The sequence of the forward primer was based on a 412 bp long contig derived from the EST-libraries which shared 99% identity at its 3' end with the partial coding sequence of the *P. somniferum* phytoene desaturase (GenBank accession no. DQ116056). The sequence of the reverse primer was designed based on the DQ116056 sequence. The PCR conditions were identical to those described above for the amplification of PSMT1 from genomic sequence except that the annealing step was carried out at 70° C. and the extension time was increased to 60 seconds.

TABLE 4

Primer combinations used to amplify PS Methyltransferases from genomic DNA

| Methyl-trans-ferase | Primer combination | Annealing tem-perature [° C.] | Ex-tension time [s] | Expected fragment size [bp] | FIG. |
|---|---|---|---|---|---|
| PSMT1 | PSMT1_F1/R2 | 62 | 60 | 739 | FIG. 5a |
| | PSMT1_F3/3R | 66 | 60 | 1568 | FIG. 5b |
| | PSMT1_F4/R4 | 68 | 60 | 318 | FIG. 5c |
| | PSMT1_F5/R5 | 63.5 | 60 | 1354 | FIG. 5d |
| | PSMT1_F6/R1 | 62.8 | 60 | 604 | FIG. 5e |

TABLE 4-continued

Primer combinations used to amplify PS Methyltransferases from genomic DNA

| Methyl-trans-ferase | Primer combination | Annealing tem-perature [° C.] | Ex-tension time [s] | Expected fragment size [bp] | FIG. |
|---|---|---|---|---|---|
| PSMT2 | PSMT2_F2/R3 | 60.3 | 60 | 613 | FIG. 10a |
| | PSMT2_F4/R4 | 60.9 | 60 | 627 | FIG. 10b |
| | PSMT2_F4/R5 | 61.7 | 60 | 909 | FIG. 10c |
| | PSMT2_F5/R6 | 62.8 | 60 | 664 | FIG. 10d |
| PSMT3 | PSMT3_F1/R1 | 68.5 | 50 | 497 | FIG. 12a |
| | PSMT3_F2/R2 | 68.5 | 50 | 564 | FIG. 12b |
| | PSMT3_F3/R3 | 68.5 | 50 | 511 | FIG. 12c |
| | PSMT3_F4/R5 | 68.5 | 50 | 589 | FIG. 12d |

Sau3AI digestion of the PCR-fragment yielded among others two fragments (280 bp and 129 bp in length) that carried BamHI-compatible sticky ends at both, their 5' and 3' ends. The 129 bp long fragment (underlined stretch in FIG. 13) was cloned into the BamHI site of the pTRV2 vector. Because Sau3AI was used to produce BamHI-compatible sticky ends, the BamHI site at the 5-end of the PDS-insert was abolished in the pYL156-PDS construct. However, the BamHI recognition site at its 3'-end was kept intact due to the nature of the PDS-insert sequence.

A sequence-confirmed pTRV2-PDS construct, with the 129 bp fragment in sense orientation, was subsequently used as a vector for generating the PSMT1 and PSMT2 silencing constructs, and served as a control in the VIGS experiments.

Generation of silencing constructs for PS PSMT1 and PSMT2 (pTRV2-PDS-PSMT1 and pTRV2-PDS-PSMT2): The DNA fragments selected for silencing PSSOMT1 and PSSOMT2 were amplified from cDNA of GSK NOSCAPINE CVS1 prepared as described above with the use of the primer sequences shown in Table 5. Additional restriction sites (forward primers: XhoI and HindIII for forward primers; KpnI site for reverse primers) were added to the gene-specific primers in order to facilitate cloning. The amplification conditions were as described above for amplifying the PDS-fragment except that the annealing temperatures were 60.9° C. for PSMT1 and 62.8° C. for PSMT2 and the extension time was 30 seconds.

TABLE 5

Primers used to amplify sequences selected for virus induced gene silencing

| Target gene to be silenced | Primer name | Oligonucleotide sequences (5'- to 3'-) (in capitals: gene-specific sequence; in lower case: added sequence; underlined: restriction sites) (SEQ ID NO:) |
|---|---|---|
| PS PHYTOENE DESATURASE | ps_pds_F | GAGGTGTTCATTGCCATGTCAA (49) |
| | ps_pds_R4 | GTTTCGCAAGCTCCTGCATAGT (50) |
| PS METHYLTRANSFERASE 1 | VIGS_PSMT1_F | aaactcgagaagctTGGTCATAATCATCAATCAG (51) |
| | VIGS_PSMT1_R | aaaggtaccCATGTACTACTACATCATCTCC (52) |
| PS METHYLTRANSFERASE 2 | VIGS_PSMT2_F | aaactcgagaagcttGTGTAACTAAGCCAGCGC (53) |
| | VIGS_PSMT2_R | aaaggtaccACTTGAATATATCACCGC (54) |

The sequence selected to silence PSMT1 (FIG. 14) was cloned into pTV00 (Ratcliff et al. (2001) Plant J. 25(2): 237-245) using HindIII and KpnI and subcloned into pTRV2-PDS using BamHI and KpnI. A sequence-confirmed pTRV2-PDS-PSMT1 construct was used in the VIGS experiments.

The sequence selected for silencing PSMT2 (FIG. 15) was cloned directly into pTRV2-PDS. Since the PCR amplification was carried out with Phusion (Finnzymes, Finland) the resulting PCR fragment carried blunt ends and, after cutting with XhoI, was cloned into pYL156-PDS cut with XhoI and SmaI. A sequence-confirmed pTRV2-PDS-PSMT2 construct was used in the VIGS experiments.

b) Transformation of Constructs into *Agrobacterium tumefaciens*

The propagation of the silencing constructs was carried out with the *E. coli* strain DH5α and, subsequently, the respective silencing constructs, as well as pTRV1 (GenBank accession no. AF406990; Liu et al. (2002) Plant J. 30(4): 415-429) were independently transformed into electrocompetent *Agrobacterium tumefaciens* (strain GV3101).

c) Infiltration of Plants

Overnight liquid cultures of *A. tumefaciens* containing each silencing construct were used to inoculate Luria-Bertani (LB) medium containing 10 mM MES, 20 μM acetosyringone and 50 μg/ml kanamycin. Cultures were maintained at 28° C. for 24 hours, harvested by centrifugation at 3000 g for 20 min, and resuspended in infiltration solution (10 mM MES, 200 μM acetosyringone, 10 mM MgCl2) to an OD600 of 2.5. *A. tumefaciens* harbouring the respective constructs (pTRV2-PDS-PSMT1, pTRV2-PDS-PSMT2 or, as a control, pTRV2-PDS) were each mixed 1:1 (v/v) with *A. tumefaciens* containing pTRV1, and incubated for two hours at 22° C. prior to infiltration. Two weeks old seedlings of GSK NOSCAPINE CVS1 grown under standard greenhouse conditions (22° C., 16 h photoperiod), with emerging first leaves, were infiltrated as described by Hagel and Facchini (2010) Nat. Chem. Biol. 6: 273-275.

d) Latex and Capsule Analysis of Silenced Plants

Leaf latex of infiltrated opium poppy plants displaying photo-bleaching as a visual marker for successful infection and silencing was analysed when the first flower buds emerged (~7 week old plants). Plants showing a similar degree of photo-bleaching of leaves were selected for analysis.

Latex was collected from cut petioles, with a single drop dispersed into 500 μL 10% acetic acid. This was diluted 10× in 1% acetic acid to give an alkaloid solution in 2% acetic acid for further analysis. Capsules were harvested by hand from glasshouse-grown from the same plants used for latex analysis and single capsules were ground in a Retsch Model MM04 ball mill into a fine powder. Ten mg samples of ground poppy straw were then weighed accurately (10±0.1 mg) and extracted in 0.5 mL of a 10% acetic acid solution with gentle shaking for 1 h at room temperature. Samples were then clarified by centrifugation and a 50 μL subsample diluted 10× in 1% acetic acid to give an alkaloid solution in 2% acetic acid for further analysis.

All solutions were analysed using a Waters Acquity UPLC system fitted with a Waters Acquity BEH C18 column, 2.1 mm×100 mm with 1.7 micron packing. The mobile phase used a gradient profile with eluent A consisting of 10 mM ammonium bicarbonate pH 10.2 and eluent B methanol. The mobile phase gradient conditions used are as listed in Table 1, with a linear gradient. The flow rate was 0.5 mL per minute and the column maintained at 60° C. The injection volume was 2 μL and eluted peaks were ionised in positive APCI mode and detected within ~3 ppm mass accuracy using a Thermo LTQ-Orbitrap. The runs were controlled by Thermo Xcalibur software.

Gradient Flow Program:

| TIME (minutes) | % Eluent A | % Eluent B | Flow (mL/ min) |
|---|---|---|---|
| 0.0 | 98.0 | 2.0 | 0.50 |
| 0.2 | 98.0 | 2.0 | 0.50 |
| 0.5 | 60.0 | 40 | 0.50 |
| 4.0 | 20.0 | 80.0 | 0.50 |
| 4.5 | 20.0 | 0.0 | 0.50 |

All data analysis was carried out in R. Putative alkaloid peaks were quantified by their pseudomolecular ion areas using custom scripts. Peak lists were compiled and any peak-wise significant differences between samples were identified using 1-way ANOVA with p-values adjusted using the Bonferroni correction for the number of unique peaks in the data set. For any peak-wise comparisons with adjusted p-values <0.05, Tukey's HSD test was used to identify peaks that were significantly different between any given sample and the control. Alkaloids were identified by comparing exact mass and retention time values to those of standards. Where standards were not available, neutral exact masses were used to generate molecular formulae hits within elemental constraints of C=1:100, H=1:200, O=0:200, N=0:3 and mass accuracy <20 ppm. The hit with the lowest ppm error within these constraints was used to assign a putative formula.

EXAMPLE 1

Assembly of Full Length PSMT1 cDNA Sequence from ESTs and Confirmation by Sequencing of Full Length cDNA The full length cDNA sequence for PSMT1 (FIG. 1*a*) was assembled from ESTs derived from the 454 sequencing platform using the CAPS sequence assembly programme. The full length cDNA sequence was confirmed by RT-PCR and direct amplification of the full length cDNA from GSK NOSAPINE CVS1 mRNA.

EXAMPLE 2

PSMT1 is Exclusively Expressed in the Noscapine Producing *Papaver somniferum* Cultivar GSK NOSAPINE CVS1

Figure 2:
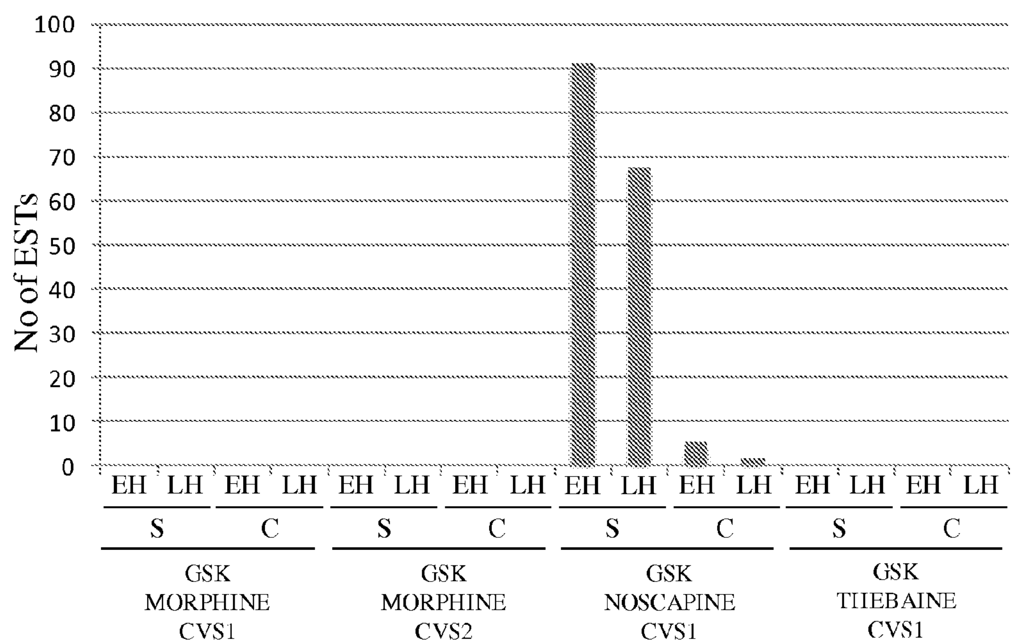
Figure 7:
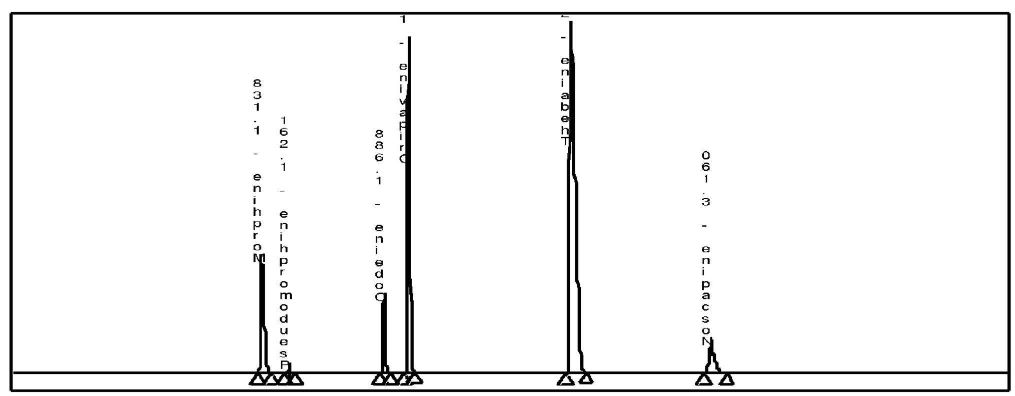
FIG. 7 illustrates a typical UPLC chromatogram for standard solution.
Figure 8:
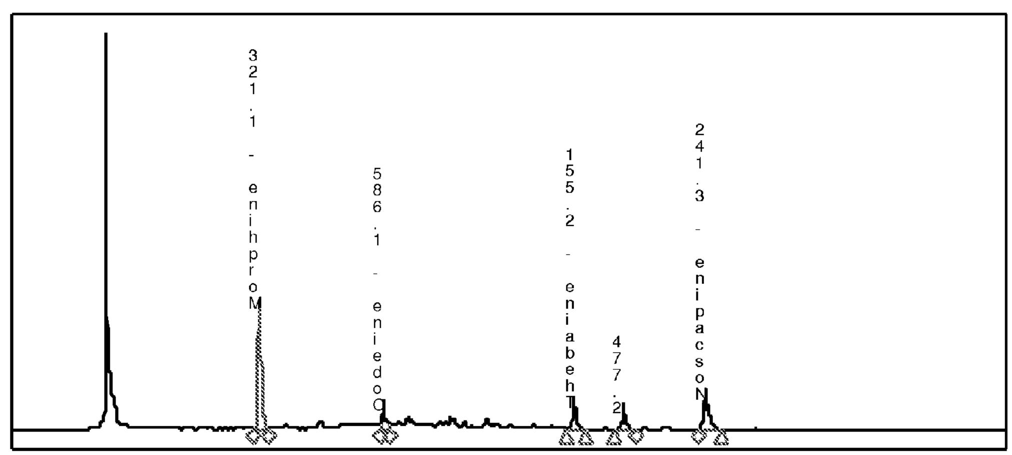
FIG. 8 illustrates a typical UPLC chromatogram for a noscapine containing poppy variety.

FIG. 2 shows the normalized distribution of ESTs associated with the PSMT1 consensus sequence across each of the 16 EST libraries prepared from two organs (capsules and stems) at two developmental stages (early and late harvest) from each of the four poppy cultivars, GSK MORHINE CVS1, GSK MORPHINE CVS2, GSK NOSAPINE CVS1 and GSK THEBAINE CVS1. ESTs corresponding to PsSOMT were exclusively found in libraries derived from the noscapine producing cultivar GSK NOSAPINE CVS1 (FIG. 2). PSMT1 expression was strongest in stem tissue shortly after flowering.

EXAMPLE 3

PCR-Amplification of PSMT1 from Genomic DNA of the Four *Papaver somniferum* Cultivars GSK NOSAPINE CVS1, GSK MORHINE CVS1, GSK MORPHINE CVS2 and GSK THEBAINE CVS1

PCR-amplifications of PSMT1 fragments were performed on genomic DNA from the four poppy cultivars GSK NOSAPINE CVS1 (noscapine cultivar), GSK MORHINE CVS1 and GSK MORPHINE CVS2 (morphine cultivars) and GSK THEBAINE CVS1 (thebaine cultivar) using the primer combinations shown in Table 2 and 3.

FIG. 5 shows the PCR-amplification of PSMT1 from genomic DNA of the four *Papaver somniferum* cultivars GSK NOSAPINE CVS1, GSK MORHINE CVS1, GSK MORPHINE CVS2 and GSK THEBAINE CVS1.

The amplification from genomic DNA yielded the gene sequence shown in FIG. 3*a*.

EXAMPLE 4

The Putative Protein Encoded by PSMT1 Shows Highest Sequence Similarity to (S)-scoulerine 9-O-methyltransferases from *Coptis japonica* and *Thalictrum flavum*

The closest homologues to the putative protein encoded by the PSMT1 open reading frame (FIG. 4) are (S)-scoulerine 9-O-methyltransferases from *Coptis japonica* (Accession: Q39522.1, Evalue: 1e-120, 61% identical) and from *Thalictrum flavum* (Accession: AAU20770.1, Evalue: 5e-118 59% identical).

EXAMPLE 5

PSMT1 is Only Present in the Genome of the Noscapine Producing *P. somniferum* Cultivar GSK NOSAPINE CVS1

The transcribed region covered by the ESTs contained the complete coding sequence of PSMT1 (including 5' and 3' untranslated regions), which was used for primer design (Table 1) to amplify the PSMT1 gene from genomic DNA in a series of overlapping fragments for sequencing (FIG. 3*a*). Upon testing a subset of the primer combinations (Table 3) on genomic DNA samples from all four cultivars it was discovered that the PSMT1 fragments could only be amplified from genomic DNA of the noscapine producing cultivar GSK NOSAPINE CVS1 but not from genomic DNA of the predominantly morphine (GSK MORHINE CVS1 and GSK MORPHINE CVS2) or thebaine (GSK THEBAINE CVS1) producing cultivars (FIG. 5). The PCR amplifications were performed on pools of genomic DNA comprising DNA from four individuals per cultivar. This discovery explains why the PSMT1 is only expressed in the GSK NOSAPINE CVS1 cultivar and is absent from the transcriptome of the other three cultivars.

EXAMPLE 6

Assembly of Full Length PSMT2 cDNA Sequence from ESTs and Confirmation by Sequencing from Genomic DNA The full length cDNA sequence for PSMT2 (FIG. 1*b*) was assembled from ESTs derived from the 454 sequencing platform using the CAPS sequence assembly programme. The full length cDNA sequence was confirmed by amplification and sequencing from genomic DNA.

EXAMPLE 7

PSMT2 is Exclusively Expressed in the Noscapine Producing *Papaver somniferum* Cultivar GSK NOSCAPINE CVS1

FIG. 9 shows the normalized distribution of ESTs associated with the PSMT2 consensus sequence across each of the 16 EST libraries prepared from two organs (capsules and stems) at two developmental stages (early and late harvest) from each of the four poppy cultivars, GSK MORPHINE CVS1, GSK MORPHINE CVS2, GSK NOSCAPINE CVS1 and GSK THEBAINE CVS1. ESTs corresponding to PSMT2 were exclusively found in libraries derived from the noscapine producing cultivar GSK NOSCAPINE CVS1. PSMT2 expression was strongest in stem tissue shortly after flowering.

EXAMPLE 8

PCR-Amplification of PSMT2 from Genomic DNA of the Four *Papaver somniferum* Cultivars GSK MORPHINE CVS1, GSK MORPHINE CVS2, GSK NOSCAPINE CVS1 and GSK THEBAINE CVS1

PCR-amplifications of PSMT2 fragments were performed on genomic DNA from the four poppy cultivars GSK MORPHINE CVS1, GSK MORPHINE CVS2, GSK NOSCAPINE CVS1 and GSK THEBAINE CVS1 using the primer combinations shown in Table 2 and 3.

FIG. 10 shows the PCR-amplification of PSMT2 from genomic DNA of the four *Papaver somniferum* cultivars GSK MORPHINE CVS1, GSK MORPHINE CVS2, GSK NOSCAPINE CVS1 and GSK THEBAINE CVS1;

The amplification from genomic DNA yielded the gene sequence shown in FIG. 3*b*.

EXAMPLE 9

The Putative Protein Encoded by PSMT2 Shows Highest Sequence Similarity to Norcoclaurine 6-O-methyltransferases from *Coptis japonica, Papaver bracteatum* and *Papaver somniferum*

The closest homologues to the putative protein encoded by the PSMT2 open reading frame (FIG. 1*b*) are (R,S)-norcoclaurine 6-O-methyltransferase from *Coptis japonica* (accession: Q9LEL6, identities: 146/355 (42%)), putative norcoclaurine 6-O-methyltransferase from *Papaver bracteatum* (accession: ACO90232, identitities: 151/346 (44%)) and S-adenosyl-L-methionine:norcoclaurine 6-O-methyltransferase from *Papaver somniferum* (accession: AAP45315, identities=148/343 (44%)). The sequence comparisons were carried out using NCBI's 'blastp' algorithm (method: compositional matrix adjust).

EXAMPLE 10

PSMT2 is Only Present in the Genome of the Noscapine Producing *P. somniferum* Cultivar GSK NOSCAPINE CVS1

The transcribed region covered by the ESTs contained the complete coding sequence of PSMT2 (including 5' and 3' untranslated regions), which was used for primer design (Table 1) to amplify the PSMT2 gene from genomic DNA in a series of overlapping fragments for sequencing (FIG. 3*b*). Upon testing a subset of the primer combinations on genomic DNA samples from all four cultivars it was discovered that the PsSOMT2 fragments could only be amplified from genomic DNA of the noscapine producing cultivar GSK NOSCAPINE CVS1 but not from genomic DNA of the predominantly morphine (GSK MORPHINE CVS1, GSK MORPHINE) or thebaine (GSK THEBAINE CVS1) producing cultivars (FIG. 10). The PCR amplifications were performed on pools of genomic DNA comprising DNA from four individuals per cultivar using primer combinations shown in Table 3. This discovery explains why the PSMT2 is only expressed in the GSK NOSCAPINE CVS1 cultivar and is absent from the transcriptome of the other three cultivars.

EXAMPLE 11

Assembly of Full Length PSMT3 cDNA Sequence from ESTs and Confirmation by Sequencing from Genomic DNA The full length cDNA sequence for PSMT3 (FIG. 1*c*) was assembled from ESTs derived from the 454 sequencing platform using the CAPS sequence assembly programme. The full length cDNA sequence was confirmed by amplification and sequencing from genomic DNA.

EXAMPLE 12

PSMT3 is Exclusively Expressed in the Noscapine Producing *Papaver somniferum* Cultivar GSK NOSCAPINE CVS1

FIG. 11 shows the normalized distribution of ESTs associated with the PSMT3 consensus sequence across each of the 16 EST libraries prepared from two organs (capsules and stems) at two developmental stages (early and late harvest) from each of the four poppy cultivars, GSK MORPHINE CVS1, GSK MORPHINE CVS2, GSK NOSCAPINE CVS1 and GSK THEBAINE CVS1. ESTs corresponding to PsSOMT3 were exclusively found in libraries derived from the noscapine producing cultivar GSK NOSCAPINE CVS1 (FIG. 11). PSMT3 expression was strongest in stem tissue shortly after flowering.

EXAMPLE 13

PCR-Amplification of PSMT3 from Genomic DNA of the Four *Papaver somniferum* Cultivars GSK MORPHINE CVS1, GSK MORPHINE CVS2, GSK NOSCAPINE CVS1 and GSK THEBAINE CVS1

PCR-amplifications of PSMT3 fragments were performed on genomic DNA from the four poppy cultivars GSK MORPHINE CVS1, GSK MORPHINE CVS2, GSK NOSCAPINE CVS1 and GSK THEBAINE CVS1 using the primer combinations shown in Table 2 and 3.

FIG. 12 shows the PCR-amplification of PSMT3 from genomic DNA of the four *Papaver somniferum* cultivars GSK MORPHINE CVS1, GSK MORPHINE CVS2, GSK NOSCAPINE CVS1 and GSK THEBAINE CVS1;

The amplification from genomic DNA yielded the gene sequence shown in FIG. 3*c*.

EXAMPLE 14

The Putative Protein Encoded by PSMT3 Shows Highest Sequence Similarity to Norcoclaurine 6-O-methyltransferases from *Papaver somniferum* and *Papaver bracteatum*

The closest homologues to the putative protein encoded by the PSMT3 open reading frame (FIG. 4) are (R,S)-norcoclaurine 6-O-methyltransferases from *Papaver somniferum* (accession: AAQ01669, identities: 275/346 (80%), *Papaver somniferum* (accession: AAP45315, identities=275/346 (80%), and *Papaver bracteatum* (accession: ACO90232, identities: 274/346 (80%)). The sequence comparisons were carried out using NCBI's 'blastp' algorithm (method: compositional matrix adjust).

EXAMPLE 15

PSMT3 is Only Present in the Genome of the Noscapine Producing *P. somniferum* Cultivar GSK NOSCAPINE CVS1

The transcribed region covered by the ESTs contained the complete coding sequence of PSMT3 (including 5' and 3' untranslated regions), which was used for primer design (Table 1) to amplify the PSMT3 gene from genomic DNA in a series of overlapping fragments for sequencing (FIG. 3*c*). Upon testing a subset of the primer combinations on genomic DNA samples from all four cultivars it was discovered that the PSMT3 fragments could only be amplified from genomic DNA of the noscapine producing cultivar GSK NOSCAPINE CVS1 but not from genomic DNA of the predominantly morphine (GSK MORPHINE CVS1, GSK MORPHINE) or thebaine (GSK THEBAINE CVS1) producing cultivars (FIG. 12). The PCR amplifications were performed on pools of genomic DNA comprising DNA from four individuals per cultivar using primer combinations shown in Table 3. This discovery explains why the PSMT3 is only expressed in the GSK NOSCAPINE CVS1 cultivar and is absent from the transcriptome of the other three cultivars.

EXAMPLE 16

Scoulerine and putative narcotoline accumulate in PSMT1- and PSMT2-silenced plants, respectively. Virus induced gene silencing led to the accumulation of scoulerine in both latex and mature capsules of PSMT1-silenced plants but not of PSMT2-silenced plants, PDS-silenced control plants or uninfected plants of GSK NOSCAPINE CVS1 (FIG. 16). Scoulerine has been shown to be an intermediate in the biosynthesis of noscapine (Battersby et al. (1968) J. Chem. Soc. (C): 2163-2172).

Putative narcotoline (4-desmethyl-noscapine) accumulated in latex and capsules of PSMT2-silenced plants but not of PSMT1-silenced plants, PDS-silenced control plants or uninfected plants of GSK NOSCAPINE CVS1 (FIG. 17).

EXAMPLE 17

PSMT1, PSMT2 and PSMT3 are Linked and Involved in Noscapine Biosynthesis

All three methyltransferase genes are present in all F2 plants that do contain noscapine. All F2 plants that do not contain the methlytransferase genes do not make noscapine (FIG. 6*a-c*).

The invention claimed is:

1. An isolated cDNA molecule that encodes a methyltransferase polypeptide, wherein said cDNA molecule comprises i) the nucleotide sequence of SEQ ID NO: 1, 2 or 3;

ii) a nucleotide sequence degenerate to the nucleotide sequence of (i);

iii) a nucleic acid sequence having at least 90% sequence identity to the full length of the cDNA sequence set forth in SEQ ID NO: 1, 2 or 3; or iv) a nucleotide sequence that encodes a methyltransferase polypeptide having at least 95% sequence identity to the full length of the protein sequence set forth in SEQ ID NO: 7, 8 or 9;

and which has retained methyl transferase activity.

2. The isolated cDNA molecule according to claim 1, wherein said cDNA molecule comprises the nucleotide sequence as set forth in SEQ ID NO: 1, 2 or 3.

3. A vector comprising the cDNA molecule according to claim 1, wherein said cDNA molecule is operably linked with a nucleic acid sequence comprising a promoter sequence.

4. The vector according to claim 3 wherein said nucleic acid sequence comprising a promoter confers constitutive expression on said methyltransferase.

5. The vector according to claim 3 wherein said nucleic acid sequence comprising a promoter confers regulated expression on said methyltransferase.

6. The vector according to claim 5 wherein said regulated expression is tissue or developmentally regulated expression.

7. The vector according to claim 5, wherein said promoter is an inducible promoter.

8. A transgenic cell transformed or transfected with the cDNA molecule of claim 1.

9. The transgenic cell according to claim 8 wherein said cell is a plant cell.

10. The transgenic cell according to claim 9 wherein said plant cell is from the family Papaveraceae.

11. The transgenic cell according to claim 10 wherein said plant cell is a *Papaver somniferum* cell.

12. A plant comprising the transgenic plant cell of claim 9.

13. The plant according to claim 12 wherein said plant is from the family Papaveraceae.

14. The plant according to claim 13 wherein said plant is *Papaver somniferum*.

15. The transgenic cell according to claim 8 wherein said cell is a microbial cell.

16. The transgenic cell according to claim 15 wherein said microbial cell is a bacterial cell.

17. The transgenic cell according to claim 15 wherein said microbial cell is a fungal cell.

18. A nucleic acid molecule comprising a transcription cassette wherein said cassette includes the nucleotide sequence set forth in SEQ ID NO: 1, 2, 3, 4, 5, or 6 nucleotide sequence or a nucleotide sequence that is at least 90% identical to the full length of the nucleotide sequence set forth in SEQ ID NO: 1, 2, 3, 4, 5, or 6, and is adapted for expression by provision of at least one promoter operably linked to said nucleotide sequence such that both sense and antisense nucleic acid molecules are transcribed from said cassette.

19. The nucleic acid molecule according to claim 18 wherein said cassette is adapted such that both sense and antisense nucleic acid molecules are transcribed from said cassette wherein said sense and antisense nucleic acid molecules are adapted to anneal over at least part or all of their length to form a siRNA or shRNA.

20. The nucleic acid molecule according to claim 18 wherein said cassette is provided with at least two promoters adapted to transcribe both sense and antisense strands of said nucleic acid molecule.

21. The nucleic acid molecule of claim 18, wherein said cassette comprises a nucleic acid molecule wherein said molecule comprises a first part linked to a second part wherein said first and second parts are complementary over at least part of their sequence and further wherein transcription of said nucleic acid molecule produces an RNA molecule which forms a double stranded region by complementary base pairing of said first and second parts thereby forming an shRNA.

22. The nucleic acid molecule of claim 18, wherein said nucleic acid molecule is part of a vector adapted for expression in a plant cell.

23. The plant cell transfected with the nucleic acid molecule of claim 18, wherein said cell has reduced expression of said methyltransferase.

24. A process for the methylation of an opiate alkaloid comprising:

cultivating the transgenic plant cell of claim 9 to produce a transgenic plant; and optionally harvesting said transgenic plant, or part thereof.

25. The process according to claim 24 wherein said harvested plant part is dried straw and said opiate alkaloid is extracted.

26. A process for the methylation of an opiate alkaloid comprising:

cultivating the transgenic microbial cell of claim 15 under conditions that methylate one or more opiate alkaloids; and optionally isolating said methylated alkaloid from the microbial cell or cell culture.

27. The process according to claim 26 wherein said microbial cell is a bacterial cell or fungal/yeast cell.

28. A method to produce a Papaveraceae plant that has altered expression of a methyltransferase comprising:

i) mutagenizing wild-type seed from a plant that does express said methyltransferase;
ii) cultivating the seed in i) to produce first and subsequent generations of plants;
iii) obtaining seed from the first generation plant and subsequent generations of plants;
iv) determining if the seed from said first and subsequent generations of plants has altered expression of said methyltransferase;
v) obtaining a sample from the first and subsequent generations of plants and
vi) analyzing a nucleic acid molecule from the plants for:
  a) a nucleic acid molecule comprising the entire nucleotide sequence shown in SEQ ID NO: 4, 5 or 6; or
  b) a nucleic acid molecule comprising a nucleotide sequence having at least 90% sequence identity to the entire nucleic acid molecule in a) and that encodes a polypeptide with methyltransferase activity; and optionally
vii) comparing the nucleotide sequence of the nucleic acid molecule in said sample to a nucleotide sequence of a nucleic acid molecule of the original wild-type plant.

29. The method according to claim 28 wherein said nucleic acid molecule from the plants is analyzed by a method comprising:

i) extracting nucleic acid from said mutated plants;
ii) amplifying a part of said nucleic acid molecule by a polymerase chain reaction;
iii) forming a preparation comprising the amplified nucleic acid and nucleic acid extracted from wild-type seed to form heteroduplex nucleic acid;
iv) incubating said preparation with a single stranded nuclease that cuts at a region of heteroduplex nucleic acid to identify the mismatch in said heteroduplex; and
v) determining the site of the mismatch in said nucleic acid heteroduplex.

30. The method according to claim 29 wherein said Papaveraceae plant has methyltransferase expression and/or activity.

31. A plant obtained by the method of claim 28.

32. A plant comprising a viral vector that includes a nucleic acid molecule, wherein said nucleic acid molecule comprises a cDNA that encodes a methyltransferase polypeptide, wherein said cDNA gene-comprises a nucleic acid molecule selected from the group consisting of:

i) a nucleic acid molecule comprising the nucleotide sequence set forth in SEQ ID NO: 1, 2 or 3;
ii) a nucleic acid molecule comprising a nucleotide sequence having at least 90% sequence identity with the entire nucleic acid molecule in (i) and which encodes a methyltransferase polypeptide; and
iii) a nucleic acid molecule that encodes a polypeptide having at least 95% amino acid sequence identity to a polypeptide comprising the amino acid sequence set forth in SEQ ID NO: 7, 8 or 9.

33. A plant comprising a viral vector, wherein said vector comprises a fragment of a cDNA sequence encoding a methyltransferase polypeptide, wherein the fragment can silence expression of the methyltransferase polypeptide, and wherein the fragment of the cDNA comprises the nucleotide sequence shown in SEQ ID NO: 11.

34. A plant comprising a viral vector, wherein said vector comprises a fragment of a cDNA sequence encoding a methyltransferase polypeptide, wherein the fragment can silence expression of the methyltransferase polypeptide, and wherein the fragment of the cDNA comprises the nucleotide sequence shown in SEQ ID NO: 12.

35. A viral vector comprising the cDNA molecule according to claim 1.

36. A method of gene silencing in a plant, comprising: introducing the viral vector of claim 35 into the plant, thereby inducing gene silencing.

37. The method of claim 36, wherein the plant is from the family Papaveraceae.

* * * * *